United States Patent [19]
Cooper, Jr.

[11] Patent Number: 6,017,883
[45] Date of Patent: Jan. 25, 2000

[54] COMPOSITION AND METHODS FOR THE INHIBITION OF PHAGOCYTES

[75] Inventor: J. Allen D. Cooper, Jr., Birmingham, Ala.

[73] Assignee: Research Corporation Technologies, Inc., Tucson, Ariz.

[21] Appl. No.: 09/033,753

[22] Filed: Mar. 3, 1998

Related U.S. Application Data

[63] Continuation of application No. 08/618,696, Mar. 20, 1996, which is a continuation of application No. 07/995,269, Dec. 21, 1992, abandoned.

[51] Int. Cl.[7] .......................... A61K 38/00; A61K 38/02; C07K 5/00; C07K 7/00
[52] U.S. Cl. ................. 514/12; 514/13; 514/14; 514/15; 514/16; 514/17; 530/333; 530/334
[58] Field of Search .................. 514/12, 13, 14, 514/15, 16, 17; 530/333, 334

[56] References Cited

FOREIGN PATENT DOCUMENTS 0403312  12/1990  European Pat. Off. ........ C12P 21/06
9116336  10/1991  WIPO ............................... C07K 5/00

OTHER PUBLICATIONS

Kalmokoff et al, *Biochem Biophys Res Comm.*, vo. 1 167, Feb. 28, 1990, pp.154–160.
Cooper et al. *Am J. Physiol.*, 260, pp. L501–L509, 1991.
Sibille et al., Am. J. Respir. Cell. Mol. Biol, vol. 1, 1989, pp. 407–416.

*Primary Examiner*—Avis M. Davenport
*Attorney, Agent, or Firm*—Scully, Scott, Murphy & Presser

[57] ABSTRACT

The present invention relates to the identification, purification and characterization of novel factors which inhibit phagocyte activation, such as inhibiting polymorphonuclear neutrophil chemotaxis, degranulation and superoxide production. Disclosed are natural peptides purified from the bronchial environment and a variety synthetic peptides and analogues designed to have enhanced or longer-lasting phagocyte-inhibiting activity. The peptides and compositions of the present invention are contemplated for use in modulating inflammatory responses in a number of clinical settings, such as in the treatment of asthma, bronchitis, acute lung injury, rheumatoid arthritis, psoriasis, dermatitis and inflammatory bowel disease, and for use as anti-proliferative agents such as in the treatment of cancer.

23 Claims, 11 Drawing Sheets

COMPOSITION AND METHODS FOR THE INHIBITION OF PHAGOCYTES

CROSS REFERENCES TO RELATED APPLICATIONS

This is a continuation of U.S. patent application Ser. No. 08/618,696 filed Mar. 20, 1996 which is a continuation of U.S. patent application Ser. No. 07/995,269 filed Dec. 21, 1992, now abandoned.

The government may own rights in the present invention pursuant Grant project #001 from the VA Merit Review.

BACKGROUND OF THE INVENTION

1. Field of the Invention

The present invention is generally directed to biological compositions and methods for inhibiting phagocyte activation, such as polymorphonuclear neutrophil (PMN) activation, as exemplified by the inhibition of PMN chemotaxis, degranulation and superoxide production. The invention concerns the purification and characterization of novel peptide factors and the generation of inhibitory synthetic peptides and analogues with enhanced inhibitory activity. The peptides of the invention are contemplated for use as anti-inflammatory agents in the treatment of diseases such as rheumatoid arthritis, dermatitis, psoriasis or inflammatory bowel disease, and more particularly, in the treatment of lung diseases such as asthma and bronchitis.

2. Description of the Related Art

Pulmonary inflammation is associated with lung damage in numerous settings. Inflammation of lung parenchyma can cause severe oxygenation impairment (Swank & Moore, 1989) while bronchial inflammation often results in narrowing of the airway luminal diameter (Snapper & Brigham, 1984). Polymorphonuclear neutrophils (PMN), important cellular constituents of acute inflammatory processes, are attracted to areas of inflammation by chemotaxins released by resident cells (Sibille & Reynolds, 1990). However, because the lung is commonly exposed by inhalation to substances, such as bacteria and dust particles, that should trigger release of these chemotaxins, a mechanism to down-regulate PMN influx is most likely present.

PMN activation occurs through an intricate cascade of chemical events that are initiated by binding of agonist to a plasma membrane receptor (Sklar, 1986). This is followed by coupling of a portion of the receptor to a GTP-binding protein with subsequent phosphorylation and activation of certain enzymes intermediate in the signal transduction process (Edelman et al., 1987). One enzyme that may be important in this process is phospholipase D (Cockcroft, 1989). The actions of phospholipase D cleavage products, I(4)P and I(4,5)$P_2$ are not well characterized although certain studies have suggested they are important in the process of PMN activation. A recent study has suggested that a specific calmodulin-dependent protein kinase, myosin light chain kinase, may phosphorylate and activate phospholipase D in PMN (Kanaho et al., 1992).

PMN, although powerful antimicrobial cells, can also cause considerable tissue damage through release of toxic molecules. The influx of PMN into lung parenchyma may be associated with acute lung injury culminating in the adult respiratory distress syndrome. Alternatively, immigration of PMN into bronchi, occurring after a number of inhalational exposures, is associated with obstruction to airflow. The influx of PMN into pulmonary parenchyma or airways is known to occur through the production of numerous agonists that attract such cells (Sibille & Reynolds, 1990). However, little is known about the mechanisms which operate to attenuate PMN influx or to inhibit PMN activation in these settings.

Influenza A virus has been shown to be capable of deactivating PMN (Hartshorn & Tauber, 1988). Previous studies have documented that PMN oxidant production, degranulation, arachidonic acid release and chemotaxis are all attenuated by cellular infection with influenza A. However, the components of influenza A virus responsible for causing these effects have not been previously described.

In addition, various host cell-derived molecules have been described that inhibit neutrophil function in vitro. These molecules include elastase and cathepsin G, which inactivate chemotactic complement activation products, specifically C5a (Brozna et al., 1977), and alpha 1 antiproteinase which inhibits PMN chemotaxis to fMLP (Stockley et al., 1990). Neutrophils and monocytes have been noted to release a low MW factor, termed neutrophil immobilizing factor, that has an apparent Mr of 5,000 daltons, is trypsin digestible, and inhibits PMN chemotaxis to a variety of agonists (Goetzl & Austen, 1972). Lymphocytes release a protein in vitro that inhibits PMN chemotaxis (Klempner & Rocklin, 1983), and adenosine, released by platelets, is also known to inhibit certain parameters of PMN activation (Cronstein et al., 1990). Shephard et al. (1989) have demonstrated that high concentrations of nonpolar proteolytic peptide fragments of C reactive protein inhibit PMN chemotaxis and oxidant production. Finally, two cyclooxygenase products, prostaglandin E (Ham et al. 1983) and prostacyclin (Kainoh et al., 1990), inhibit PMN chemotaxis.

Molecules which inhibit phagocyte activation, such as inhibiting PMN function, have potential for use as anti-inflammatory and anti-proliferative agents. They would be particularly useful for treating a variety of lung diseases and disorders,-for example, asthma, bronchitis and acute lung injury. However, as phagocytes in general, and PMN in particular, are intimately involved in various immune and inflammatory responses, phagocyte inhibitors would also be suitable for reducing inflammation in other clinical settings, such as in the treatment of rheumatoid arthritis, inflammatory bowel disease, reperfusion cardiac damage after myocardial infarction, and various dermatological diseases such as psoriasis and dermatitis.

Unfortunately, the molecules documented to inhibit phagocyte and neutrophil function to date suffer from certain drawbacks that limit their potential for clinical use. For example, several of the potential PMN inhibitors described above have only been poorly characterized and have not been purified. In common with various cytokines, PMN inhibitors have a low abundance in biological systems and are therefore unlikely to be obtainable in quantities sufficient for clinical use from natural sources. Other effector molecules may not be suitable for clinical use due to, for example, high concentrations necessary to achieve inhibition, or a lack of defined biological specificity. Furthermore, although the mediators described above have anti-inflammatory properties in vitro, there are few investigations examining in vivo significance in the pulmonary setting.

Therefore, there currently exists in the art a need for the identification and characterization of phagocyte and PMN inhibitors, and particularly, those PMN inhibitors which can be produced in significant quantities. Elucidating the mechanism of action of a PMN inhibitor would provide further advantages, and the discovery of a molecule which inhibits PMN function at a central point in signal transduction would represent a significant breakthrough in the development of effective anti-inflammatory agents. The identification and production of a PMN inhibitor would lead to the development of anti-inflammatory agents particularly suitable for use in treating diseases associated with pulmonary inflammation, such as asthma, chronic bronchitis and acute lung injury.

SUMMARY OF THE INVENTION

The present invention addresses these and other drawbacks in the prior art by providing compositions and methods for inhibiting phagocyte activation, such as inhibiting polymorphonuclear neutrophil (PMN) functions, including oxidant production, degranulation and chemotaxis. The invention is directed to the purification and characterization of peptide factors with neutrophil inhibiting activity, and more particularly, to synthetic peptides with such activity and enhanced or longer-lasting inhibitory activity. The peptides of the present invention are contemplated for use as anti-inflammatory therapeutic agents, and particularly, for use in the treatment of lung diseases such as asthma and bronchitis.

The peptide factors of the present invention are generally referred to herein as polymorphonuclear neutrophil inhibitor peptides, or simply, neutrophil inhibitor peptides (NIPs).

Disclosed herein are methods for purifying such peptides from natural sources, for example, from bronchoalveolar lavage fluid, and the sequences of such native inhibitory peptides. In that the first native peptide to be characterized in this manner has the sequence (from the N- to the C-terminal): Arg-Glu-Gly-Ser-Tyr-Phe-Phe-Gly-Asp-Asn-Ala (seq id no:1), native or synthetic peptides having this 11 amino acid sequence are referred to herein as NIP. A second native peptide was also purified and found to have the truncated 10 amino acid sequence: Glu-Gly-Ser-Tyr-Phe-Phe-Gly-Asp-Asn-Ala (seq id no:2), this peptide and synthetic peptides with this sequence have been termed NIP-Arg.

Synthetic peptides with sequences corresponding to those of the native 11 and 10 amino acid peptides were found to have phagocyte inhibitory activity, demonstrated by inhibiting PMN functions, such as chemotaxis and oxidant production. A truncated synthetic peptide with the 5 amino acid sequence Gly-Ser-Tyr-Phe-Phe (seq id no:3) was also found to inhibit PMN 30 chemotaxis with approximately the same potency as NIP. Three second generation peptides Gly-Ala-Ala-Phe-Phe (seq id no:12), Gly-Ser-Ala-Phe-Phe (seq id no:13) and Gly-Ala-Tyr-Phe-Phe (seq id no:14) were also found to have inhibitory activity. As such, the invention particularly pertains to peptides which inhibit PMN activation and include within their sequence the sequence Gly-Ser-Tyr-Phe-Phe (seq id no:3), or the sequences Glu-Gly-Ser-Tyr-Phe-Phe-Gly-Asp-Asn-Ala (seq id no:2), Arg-Glu-Gly-Ser-Tyr-Phe-Phe-Gly-Asp-Asn-Ala (seq id no:1); and also the peptides including the sequences Gly-Ala-Ala-Phe-Phe (seq id no:12), Gly-Ser-Ala-Phe-Phe (seq id no:13) or Gly-Ala-Tyr-Phe-Phe (seq id no:14).

Two designations for amino acids are used interchangeably throughout this application, as is common practice in the art. Alanine=Ala (A); Arginine=Arg (R); Aspartate=Asp (D); Asparagine=Asn (N); Cysteine=Cys (C); Glutamate=Glu (E); Glutamine=Gln (Q); Glycine=Gly (G); Histidine=His (H); Isoleucine=Ile (I); Leucine=Leu (L); Lysine=Lys (K); Methionine=Met (M); Phenylalanine=Phe (F); Proline=Pro (P); Serine=Ser (S); Threonine=Thr (T); Tryptophan=Trp (W); Tyrosine=Tyr (Y); Valine=Val (V).

The sequences of NIP and NIP-Arg, as purified from bronchoalveolar lavage fluid, contain a potential phosphorylation site comprising glycine, serine and tyrosine, either or both of which serine and tyrosine residues have the potential to become phosphorylated. Indeed, it is shown herein that NIP and the truncated synthetic peptide Gly-Ser-Tyr-Phe-Phe (seq id no:3) are actively phosphorylated by PMN lysates. The inventor proposes that NIP and NIP-like peptides and derivatives may be phosphorylated as part of their mechanism of action, and further, that such phosphorylation may result in the reduction of their inhibitory actions. Therefore, an important aspect of the present invention is to provide second generation peptides with enhanced or longer-lasting inhibitory activity. Such improved peptides will generally have sequences based upon the core sequence of NIP, namely Gly-Ser-Tyr-Phe-Phe, but will contain modifications in those residues serine, tyrosine, and also glycine, which form both the target and additional recognition elements of the phosphorylation site. These aspects of the invention are represented in exemplary embodiments by the peptides Gly-Ala-Ala-Phe-Phe (seq id no:12), Gly-Ser-Ala-Phe-Phe (seq id no:13) and Gly-Ala-Tyr-Phe-Phe (seq id no:14).

Accordingly, in important embodiments, the present invention is directed to peptides of between five and about 100 amino acid residues in length which include within their sequence an amino acid sequence represented by $AA_1$-$AA_2$-$AA_3$-Phe-Phe, wherein $AA_1$ is glycine or a biologically functional equivalent thereof; $AA_2$ is serine or a biologically functional equivalent thereof; and $AA_3$ is tyrosine or a biologically functional equivalent thereof.

The invention is further directed to peptides of between five and about 100 amino acid residues in length which include within their sequence an amino acid sequence represented by Glu-$AA_1$-$AA_2$-$AA_3$-Phe-Phe-Gly-Asp-Asn-Ala, or more preferably, a sequence represented by Arg-Glu-$AA_1$-$AA_2$-$AA_3$-Phe-Phe-Gly-Asp-Asn-Ala; wherein $AA_1$ is glycine or a biologically functional equivalent thereof; $AA_2$ is serine or a biologically functional equivalent thereof; and $AA_3$ is tyrosine or a biologically functional equivalent thereof.

The sequence of NIP was found to be highly homologous to the following stretch of amino acids contained within influenza A nucleoprotein: Asn-Glu-Gly-Ser-Tyr-Phe-Phe-Gly-Asp-Asn-Ala (seq id no:16). Influenza A has generally been shown to be capable of deactivating PMN, although the components of the virus that mediate these effects were not known prior to the present invention. However, by identifying sequences capable of inhibiting PMN in a functionally similar manner to influenza A viruses, and by showing their homology with the above stretch of influenza A nucleoprotein, the inventor has, for the first time, defined a precise element of influenza A which acts to inhibit PMN. As such, this invention is also directed to peptides of between five and about 100 amino acid residues in length which include within their sequence an amino acid sequence represented by Asn-Glu-$AA_1$-$AA_2$-$AA_3$-Phe-Phe-Gly-Asp-Asn-Ala; wherein $AA_1$ is glycine or a biologically functional equivalent thereof; $AA_2$ is serine or a biologically functional equivalent thereof; and $AA_3$ is tyrosine or a biologically functional equivalent thereof.

As stated above, one intention of the present invention is to provide peptides with sequences based upon that of the NIP core sequence, but with enhanced or longer-acting inhibitory activity. Such peptides may be referred to as second generation peptides, engineered or modified peptides, or peptide analogues or variants. It is particularly contemplated that improvements in activity may be achieved by substituting one or more of the glycine, serine or tyrosine residues which form the recognition and target elements of the phosphorylation site with a distinct amino acid.

In general, it is contemplated that the glycine, serine or tyrosine residues of the phosphorylation site may be exchanged, or substituted, for any other amino acid residue. However, in preferred embodiments, it is contemplated that certain advantages may be found in substituting one of these residues for a biologically functional equivalent amino acid. The concept of biologically functional equivalent amino acids is well known to those of skill in the art, and is embodied in the knowledge that modifications and changes may be made in the structure of a protein or peptide and still obtain a molecule having like or otherwise desirable characteristics.

It is known that certain amino acids may be substituted for other amino acids in a protein or peptide structure without appreciable loss of function, as may be measured by the interactive binding capacity for structures such as substrates or enzymes, and the ability to compete with other molecules for binding to these sites. Since it is the interactive and competitive capacity of a protein or peptide that defines its biological functional activity, certain amino acid substitutions can be made in a peptide sequence (or, of course, its underlying DNA coding sequence) and nevertheless obtain a peptide with like, or even improved properties.

Amino acid substitutions are generally based on the relative similarity of the amino acid side-chain substituents, for example, their hydrophobicity, hydrophilicity, charge, size, and the like. An analysis of the size and shape of the amino acid side-chain substituents reveals that alanine, glycine and serine all have a very similar size, and that phenylalanine, tryptophan and tyrosine all have a similar shape. Therefore, based upon these considerations, alanine, glycine and serine, and phenylalanine, tryptophan and tyrosine, are defined herein as biologically functional equivalents.

To effect more quantitative changes, the hydropathic index of amino acids may be considered. The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Substitution of like amino acids can also be made on the basis of hydrophilicity, as disclosed in U.S. Pat. No. 4,554,101, incorporated herein by reference. In U.S. Pat. No. 4,554,101, the following hydrophilicity values are assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent protein.

The term "biologically functional equivalent of glycine, serine or tyrosine" is used herein to refer to an amino acid which has either a hydropathicity or hydrophilicity value of within ±2.0 of the hydropathicity or hydrophilicity values of glycine, serine or tyrosine. Thus, from the values presented above and known in the art, it can readily be seen that equivalents of glycine include alanine, threonine, serine, tryptophan, tyrosine, proline, asparagine, glutamine, histidine, cysteine, methionine, valine, leucine and isoleucine. Likewise, equivalents of serine include glycine, threonine, tryptophan, tyrosine, proline, asparagine, glutamine, alanine, histidine, cysteine, methionine, and valine; and equivalents of tyrosine include phenylalanine, glycine, threonine, serine, tryptophan, proline, histidine, asparagine, glutamine, alanine, cysteine, methionine, valine, leucine and isoleucine.

The present invention is therefore further directed to peptides of between five and about 100 amino acid residues in length which include within their sequence an amino acid sequence represented by $AA_1$-$AA_2$-$AA_3$-Phe-Phe; Glu-$AA_1$-$AA_2$-$AA_3$-Phe-Phe-Gly-Asp-Asn-Ala; Arg-Glu-$AA_1$-$AA_2$-$AA_3$-Phe-Phe-Gly-Asp-Asn-Ala; or Asn-Glu-$AA_1$-$AA_2$-$AA_3$-Phe-Phe-Gly-Asp-Asn-Ala; wherein $AA_1$ is glycine, alanine, tryptophan, proline, asparagine, glutamine, histidine, cysteine, methionine, valine, leucine, isoleucine, threonine, serine or tyrosine; $AA_2$ is serine, alanine, glycine, tryptophan, proline, asparagine, glutamine, histidine, cysteine, methionine, valine, threonine or tyrosine; and $AA_3$ is tyrosine, alanine, glycine, tryptophan, proline, histidine, asparagine, glutamine, cysteine, methionine, valine, phenylalanine, leucine, isoleucine, serine or threonine.

It will be understood that further additional considerations may be brought to bear when choosing an appropriate biologically functional equivalent substitution for glycine, serine or tyrosine from the list of alternatives presented above. For example, one may choose not to employ threonine as an alternative residue in any position, particularly as a substitute for serine or tyrosine, as this residue has the potential to become phosphorylated. Equally, for the same reasons, one may choose not to employ serine or tyrosine in other positions within the peptide. However, the mechanism of action may prove to involve kinases which do not phosphorylate threonine, when the use of this residue as a biological equivalent would still be appropriate. Furthermore, it will be understood that the utility of the peptides of the present invention is not limited to the inhibition or PMN activation and threonine functional equivalents may be used in other embodiments, such as in antibody production.

In any event, preferred embodiments of the invention are directed to peptides of between five and about 100 amino acid residues in length which include within their sequence an amino acid sequence represented by $AA_1$-$AA_2$-$AA_3$-Phe-Phe; Glu-$AA_1$-$AA_2$-$AA_3$-Phe-Phe-Gly-Asp-Asn-Ala; Arg-Glu-$AA_1$-$AA_2$-$AA_3$-Phe-Phe-Gly-Asp-Asn-Ala; or Asn-Glu-$AA_1$-$AA_2$-$AA_3$-Phe-Phe-Gly-Asp-Asn-Ala; wherein $AA_1$ is glycine, alanine, tryptophan, proline, asparagine, glutamine, histidine, cysteine, methionine, valine, leucine or isoleucine; $AA_2$ is serine, alanine, glycine, tryptophan, proline, asparagine, glutamine, histidine, cysteine, methionine or valine; and $AA_3$ is tyrosine, alanine, glycine, tryptophan, phenylalanine, proline, histidine, asparagine, glutamine, cysteine, methionine, valine, leucine or isoleucine.

In even more preferred embodiments, it is contemplated that the use of alanine would be appropriate as a substitute for glycine, serine or tyrosine. As alanine is a small, neutral amino acid this renders it a particularly preferred substitute, or replacement, which is highly unlikely to substantially alter the various properties of the peptide in question other than its ability to become phosphorylated. Thus the invention is even more preferably directed to peptides of between five and about 100 amino acid residues in length which include within their sequence an amino acid sequence represented by $AA_1$-$AA_2$-$AA_3$-Phe-Phe; Glu-$AA_1$-$AA_2$-$AA_3$-Phe-Phe-Gly-Asp-Asn-Ala; Arg-Glu-$AA_1$-$AA_2$-$AA_3$-Phe-Phe-Gly-Asp-Asn-Ala; or Asn-Glu-$AA_1$-$AA_2$-$AA_3$-Phe-Phe-Gly-Asp-Asn-Ala; wherein $AA_1$ is glycine or alanine; $AA_2$ is serine or alanine; and $AA_3$ is tyrosine or alanine.

It will be understood that peptides in accordance with the present invention may variously include additional sequences other than those outlined above and the biological functional equivalents thereof. For example, if isolated from a natural source, such as, for example, from bronchoalveolar lavage fluid, cell culture supernatants, or even from influenza A virus or influenza A virus nucleoprotein, they may include various other naturally-occurring amino acid sequences up to a total length of about 100 amino acids.

Furthermore, peptides may be prepared, by synthetic or recombinant means, which also include various sequences in addition to those described above. Such peptides may be designed, or engineered, to include multiple copies of the sequences of the present invention. Alternatively, other elements, for example, those designed to impart targeting functions to the peptide may be included, as may elements designed to enhance peptide stability, as is discussed more fully below.

However, as is generally understood in the art, there are many advantages to using smaller peptides in human therapy as opposed to the larger peptides and polypeptides of about 100 amino acids. These include, for example, the cost and relative ease of large scale synthesis, and improved pharmacological properties such as the ease with which they can penetrate tissues and their low immunogenicity. Therefore, in certain embodiments, peptides which include a sequence in accordance with those described above and which are between five and about 50 amino acid residues in length are preferred, those of between five and about 20 amino acid residues in length are more preferred, and those of between five and 11 amino acid residues in length are even more preferred.

Accordingly, in certain aspects, this invention is directed to peptides having a sequence in accordance with the amino acid sequences of seq id no:1, seq id no:2, seq id no:3 or seq id no:16, and analogues of these sequences in which one or more residues within the phosphorylation site have been substituted by alanine. These amino acid sequences are represented by those set forth below, of which seq id no:12, seq id no:13 and seq id no:14 are currently preferred:

Arg-Glu-Gly-Ser-Tyr-Phe-Phe-Gly-Asp-Asn-Ala (seq id no:1)
Arg-Glu-Gly-Ala-Ala-Phe-Phe-Gly-Asp-Asn-Ala (seq id no:4)
Arg-Glu-Gly-Ser-Ala-Phe-Phe-Gly-Asp-Asn-Ala (seq id no:5)
Arg-Glu-Gly-Ala-Tyr-Phe-Phe-Gly-Asp-Asn-Ala (seq id no:6)
Arg-Glu-Ala-Ser-Tyr-Phe-Phe-Gly-Asp-Asn-Ala (seq id no:7)
Glu-Gly-Ser-Tyr-Phe-Phe-Gly-Asp-Asn-Ala (seq id no:2)
Glu-Gly-Ala-Ala-Phe-Phe-Gly-Asp-Asn-Ala (seq id no:8)
Glu-Gly-Ser-Ala-Phe-Phe-Gly-Asp-Asn-Ala (seq id no:9)
Glu-Gly-Ala-Tyr-Phe-Phe-Gly-Asp-Asn-Ala (seq id no:10)
Glu-Ala-Ser-Tyr-Phe-Phe-Gly-Asp-Asn-Ala (seq id no:11)
Gly-Ser-Tyr-Phe-Phe (seq id no:3)
Gly-Ala-Ala-Phe-Phe (seq id no:12)
Gly-Ser-Ala-Phe-Phe (seq id no:13)
Gly-Ala-Tyr-Phe-Phe (seq id no:14)
Ala-Ser-Tyr-Phe-Phe (seq id no:15)
Asn-Glu-Gly-Ser-Tyr-Phe-Phe-Gly-Asp-Asn-Ala (seq id no:16)
Asn-Glu-Gly-Ala-Ala-Phe-Phe-Gly-Asp-Asn-Ala (seq id no:17)
Asn-Glu-Gly-Ser-Ala-Phe-Phe-Gly-Asp-Asn-Ala (seq id no:18)
Asn-Glu-Gly-Ala-Tyr-Phe-Phe-Gly-Asp-Asn-Ala (seq id no:19)
Asn-Glu-Ala-Ser-Tyr-Phe-Phe-Gly-Asp-Asn-Ala (seq id no:20)

It is further contemplated that any peptide of the present invention may be modified to render it biologically protected. As is generally known in the art, biologically protected peptides have certain advantages over unprotected, i.e., unmodified, peptides when administered to human subjects. As disclosed in U.S. Pat. No. 5,028,592, incorporated herein by reference, a peptide which is protected, for example, through acylation of the amino terminus and/or amidation of the carboxyl terminus often exhibits an increase in pharmacological activity.

Bioactive peptides which contain an acetyl group bound to the N-terminus and/or an amido function bound to the C-terminus have been found to maintain biological activity, but to be less susceptible to acid hydrolysis. This is believed to be due, in part, to the protecting groups playing a role in reducing the susceptibility of the protected peptide to enzymatic attack and degradation. Thus all biologically protected or modified peptides are intended to fall within the scope of the present invention.

In other preferred embodiments, the invention is directed to peptides being of between five and about 100 amino acid residues in length, capable of inhibiting phagocyte, and particularly, polymorphonuclear neutrophil activation, which peptides include within their sequence an amino acid sequence represented by $AA_1$-$AA_2$-$AA_3$-Phe-Phe, wherein $AA_1$ is glycine or alanine; $AA_2$ is serine or alanine; and $AA_3$ is tyrosine or alanine. Representative peptides include Gly-Ser-Tyr-Phe-Phe (seq id no:3); Arg-Glu-Gly-Ser-Tyr-Phe-Phe-Gly-Asp-Asn-Ala (seq id no:1); Glu-Gly-Ser-Tyr-Phe-Phe-Gly-Asp-Asn-Ala (seq id no:2); Asn-Glu-Gly-Ser-Tyr-Phe-Phe-Gly-Asp-Asn-Ala (seq id no:16); Gly-Ala-Ala-Phe-Phe (seq id no:12); Gly-Ser-Ala-Phe-Phe (seq id no:13); and Gly-Ala-Tyr-Phe-Phe (seq id no:14).

As used herein, the term "capable of inhibiting phagocyte activation" is intended to refer to the capacity of a given peptide, peptide analogue or composition to inhibit phagocyte activation to any detectable degree, i.e. to reduce activity below the levels observed in the absence of the peptide composition. The term "phagocytes" refers to cells capable of engulfing and ingesting particles, such as, for example, macrophages, eosinophils, monocytes, and particularly, polymorphonuclear neutrophils (PMN).

The capacity to inhibit phagocyte, and particularly, polymorphonuclear neutrophil, activation may be characterized by any one of a variety of parameters, such as, for example, the inhibition of oxidant production or degranulation, and particularly, the inhibition of chemotaxis. Various assays may be used to determine such activation, including the in vitro assays disclosed herein, and any modifications thereof which will generally be known to those of skill in the art. For example, the inhibition of PMN chemotaxis may be determined using fMLP, recombinant C5a, or leukotriene $B_4$ (cooper et al., 1991), and PMN superoxide production may be measured using an assay utilizing the reduction of ferricytochrome C by superoxide (Cooper et al. (1988). The use of in vivo assays such as the model of dermal inflammation in rabbits described herein is also contemplated.

The preferred method for preparing peptides in accordance with the present invention is contemplated to be via automated peptide synthesis. A synthetic peptide may be straightforwardly prepared using an automated peptide synthesizer, the operation of which will be generally known to those of skill in the art. Alternatively, peptides in accordance with the invention may be purified from a natural source, such as, for example, from bronchoalveolar lavage fluid, cell culture supernatants, or even from influenza A virus or influenza A virus nucleoprotein.

Peptides may also by prepared by recombinant means, and the "recombinant" peptide obtained from recombinant host cells which express the peptide. To achieve this, one would prepare a specific oligonucleotide, based upon the sequence of the desired peptide, as is known to those of skill in the art, and then insert the oligonucleotide into an expression vector, such as any one of the many expression vectors currently available commercially. One would then transform a prokaryotic or eukaryotic host cell with the vector, where it will direct the expression of the so-called recombinant version of the peptide, which may then be purified from the recombinant host cell.

Further aspects of this invention concern methods for the preparation of a phagocyte inhibitor, such as a polymorphonuclear neutrophil inhibitor, and compositions comprising a phagocyte inhibitor, purified relative to its natural state. The term "purified relative to its natural state", as used herein, is intended to refer to an inhibitor composition which has been subjected to fractionation to remove various non-inhibitor components, and which composition substantially retains its phagocyte inhibitory activity. A preferred sources for isolating such a phagocyte inhibitor is bronchoalveolar lavage. However, other sources are also contemplated, such as, for example, recombinant host cells expressing such peptides; cell culture supernatants, and particularly, culture supernatants from cells of pulmonary origin; or even influenza A virus or compositions containing influenza A virus nucleoprotein.

To prepare a phagocyte inhibitor such as a polymorphonuclear neutrophil inhibitor in accordance with the present invention, one would obtain a natural source of the inhibitor, preferably bronchoalveolar lavage fluid from an animal, subject this material or fluid to fractionation, and identify a fraction(s) containing phagocyte inhibitory activity, for example, using any of the assays disclosed herein. The number of fractionation steps employed being dependent on the degree of purification desired and the intended use of the resultant inhibitor, for example, clinical, analytical, antigenic, etc.

Preferred methods for the preparation of a phagocyte inhibitor from natural sources include subjecting the starting material to fractionation according to charge and hydrophobicity. A particularly preferred purification method, based upon the use of C18 cartridges, followed by preparative isoelectric focusing and reverse phase high performance liquid chromatography (RPHPLC), is disclosed in detail herein. The use of a pH gradient ranging from 4–6 is preferred in the isoelectric focusing, and the use of elution buffers with an increasing gradient of organic compounds, such as increasing acetonitrile concentrations, is preferred in the RPHPLC.

However, the best mode presently known by the inventor to prepare an inhibitory peptide in accordance with the present invention remains automated peptide synthesis. There are many advantages to using synthetic peptides, especially small peptides, instead of compositions purified from nature. These include, for example, the cost and relative ease of large scale synthesis, as opposed to purification from natural sources; the invariant composition of the purified peptides obtained from different syntheses; and the elimination of the possibility that any other natural factors or compounds may be present which may adversely affect activity despite their low concentration. Moreover, in regard to the treatment aspects of this invention, peptides have the further preferable properties of having low immunogenicity and of penetrating tissues easily. The latter is particularly true in the present case due to the non-polar nature of the peptides in question.

The peptides and compositions of the present invention are envisioned to be of use in a number of different embodiments. Importantly, these novel peptide inhibitors are contemplated for use as anti-inflammatory molecules in various clinical settings. For example, they may be used in treating acute lung injury and inflammatory diseases such as rheumatoid arthritis, inflammatory bowel disease, reperfusion cardiac damage after myocardial infarction. They are thought to be particularly suitable for treating asthma and bronchitis. These peptides could even be used as antiproliferative agents to downregulate lymphocyte proliferation, for example, in the treatment of cancer and other diseases and disorders associated with increased cellular proliferation.

As such, further aspects of the present invention concern pharmaceutical compositions which comprise a peptide in accordance with the present invention in a pharmaceutically acceptable excipient. These compositions include formulations for parenteral administration, such as for intravenous, intramuscular, subcutaneous and intraperitoneal administration; inhalants, aerosols and spay formulations; formulations of peptides for topical use, such as in creams, ointments and gels; and liposome-encapsulated peptides.

For the treatment of asthma and bronchitis, one may use nasal solutions or sprays, aerosols or inhalants. Sprays, aerosols and inhalants, are only effective if the droplets are sufficiently fine and uniform in size so that the mist reaches the bronchioles. Particle size is of major importance in the administration of therapeutic agents via aerosols or inhalants. The optimum particle size for penetration into the pulmonary cavity is of the order of 0.5 to 7 $\mu$m. As fine mists are produced by pressurized aerosols, their use is considered advantageous.

Formulations for parenteral administration may generally include solutions of the peptide inhibitor in sesame or peanut oil, aqueous propylene glycol, or in sterile aqueous solutions. Such aqueous solutions should be suitably buffered if necessary and the liquid diluent first rendered isotonic with sufficient saline or glucose. The precise compositions and use of such pharmaceutical carriers will generally be known to those of skill in the art in light of the present disclosure. For a detailed listing of suitable pharmaceutical agent/additives compositions and associated administrative techniques one may wish to refer to *Remington's Pharmaceutical Sciences,* 16th ed., 1980, Mack Publishing Co., incorporated herein by reference.

For the direct delivery of the inhibitory peptides to tissues other than pulmonary tissues, it is contemplated that liposome-encapsulated forms may be employed. Such techniques are known to increase the efficacy and significantly prolong the half-life of administered compounds, and particularly, compounds of lower molecular weight such as the peptides disclosed herein. Various techniques for liposome encapsulation exist and will be generally be known to those of skill in the art.

In further embodiments, the present invention is directed to methods for inhibiting phagocyte, and particularly, polymorphonuclear neutrophil activation, comprising contacting the phagocytes or polymorphonuclear neutrophils with a peptide or composition in accordance with the present invention in an amount effective to inhibit their activation. The phagocytes or polymorphonuclear neutrophils may either be in vitro or may be located within an animal, in which case, they may be contacted by administering the peptides or composition to the animal.

Still further embodiments of the invention are methods for reducing inflammation in an animal, comprising administering to an animal with inflammation a therapeutically effective amount of a pharmaceutical composition comprising a peptide or composition in accordance with the present invention. As discussed above, the inflammatory conditions which may be treated in this manner include rheumatoid arthritis, inflammatory bowel disease, reperfusion cardiac damage, and particularly, asthma and bronchitis. Any type of pharmaceutical composition may be employed, such as parenteral compositions; inhalants, aerosols and spay formulations; creams, ointments and gels; and liposome-encapsulated formulations.

In addition to their therapeutic uses, the peptides of the present invention will have utility in other embodiments. These include, for example, their use in various bioassays such as, as positive controls in assays of chemotaxis inhibitors. They may also be used as antigens to raise polyclonal antisera, or ultimately, to generate specific monoclonal antibodies. Antibodies against NIP and NIP-based peptides could be used in expression cloning, and may also prove to be of value in determining biological levels of NIP and in documenting the ability of patients' cells to produce NIP. As NIP levels may correlate with certain lung disorders, anti-NIP antibodies have potential as valuable diagnostic tools.

For example, the relative concentration of NIP in tissue may correlate with subsequent development of inflammatory disorders such as bronchitis, acute lung injury, arthritis, inflammatory bowel disease or psoriasis. Previous work with the natural molecule has shown such a correlation, i.e., the degree of bronchitis induced by inhalation of a substance was inversely proportional to the concentration of NIP present in the bronchial secretions prior to the challenge (Cooper et al., 1991). Therefore, diagnostic tests to measure concentrations of NIP in the airways or other tissues may be useful for predicting development or prognosis of disease.

Moreover, the peptide sequences of this invention are contemplated for use in designing oligonucleotide probes or primers. These may used, for example, in Southern or Northern blotting to examine the tissue distribution and/or expression of NIP, or in the molecular cloning of cDNAs or genes encoding NIP polypeptides or related proteins including NIP-homologous sequences. "Cloning" NIP peptides or related proteins, refers to the process of obtaining a specific DNA molecule encoding such a peptide or protein, in a form distinct from other portions of DNA. To achieve this, one may screen CDNA or genomic libraries with oligonucleotide probes designed from a knowledge of the amino acid sequences disclosed herein, and preferably, designed from seq id no:1.

DETAILED DESCRIPTION OF THE PREFERRED EMBODIMENTS

Figure 1:
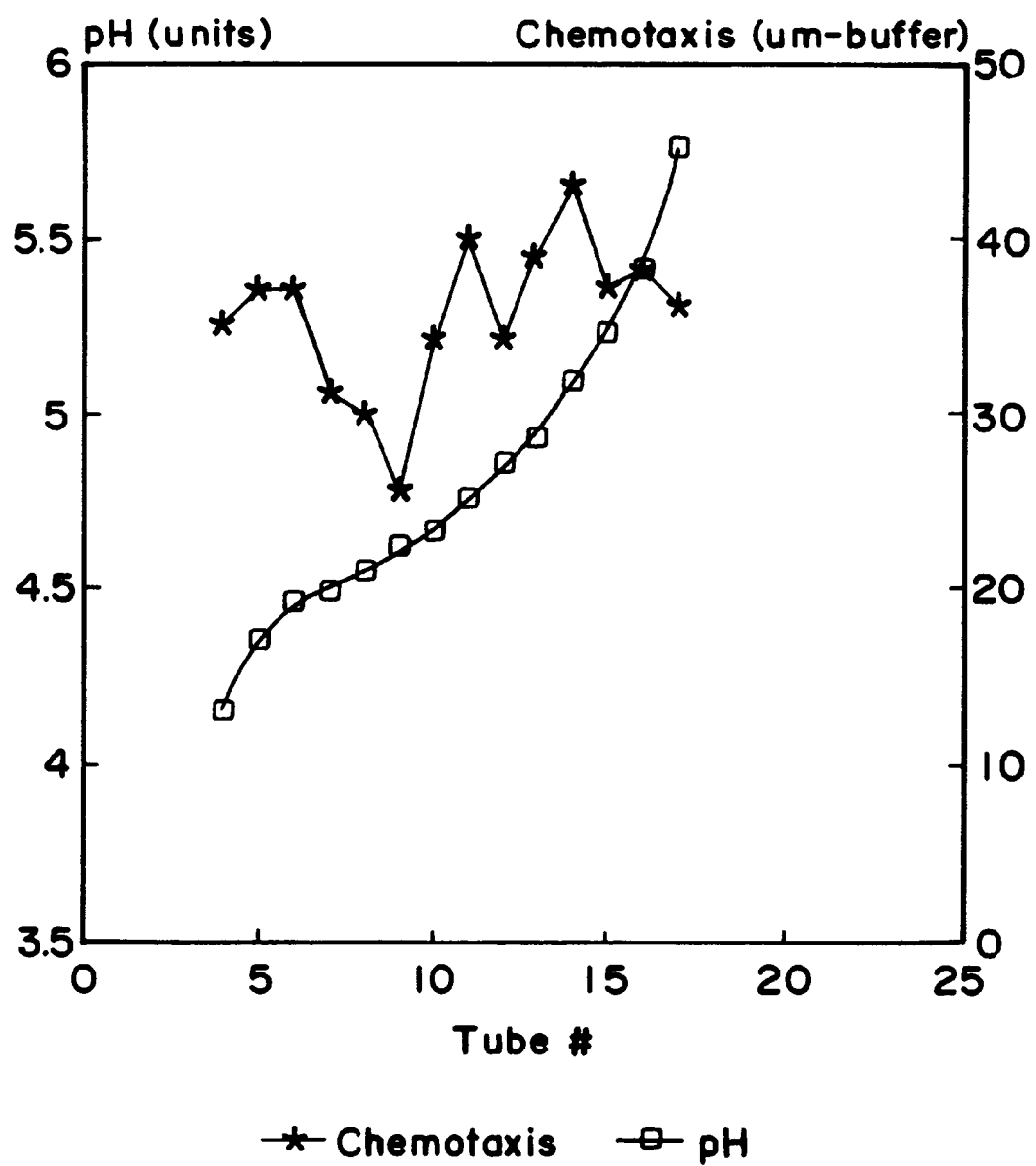
FIG. 1. Fractionation of bronchoalveolar lavage by isoelectric focusing after preparation using C18 cartridges. Fractions at varying pH (left ordinate) were diluted 1:1000 into 10 nM C5a and chemotactic activity was assessed. Chemotaxis is expressed as distance migrated in $\mu$m minus the distance migrated to buffer alone. Each point represents the mean of triplicate determinations. Standard deviation varied less than 10%. Similar results were noted during 5 other separated isoelectric focusing runs.

Pulmonary inflammation is known to be associated with various forms of lung damage. Polymorphonuclear neutrophils (PMN) are important cellular constituents of acute inflammatory processes and are attracted to areas of inflammation by chemotaxins released by resident cells (Sibille & Reynolds, 1990). Although activation of PMN is essential to many processes, these cells can also cause tissue damage by releasing toxic molecules. Thus activated PMN can contribute to disorders such as adult respiratory distress syndrome and cause airflow obstruction.

Late phase reactions, occurring in skin (Solley et al., 1976) and bronchi after exposure to antigen are histologically characterized by inflammation and edema. Similar reactions may occur after exposure to other inhaled substances such as isocyanates (Gordon et al., 1985), extracts of cotton bract (cooper et al., 1986), ozone (Holtzman et al., 1983) and others. In all of these situations increased numbers of inflammatory cells in the airways have been documented and reductions in flow rates can occur at variable time points after inhalation. Unlike bronchospasm due to pure muscle contraction, airway narrowing associated with inflammation is more slowly reversible.

Acute lung injury, occurring after a number of stimuli, is commonly associated with increased numbers of PMN in the lung parenchyma. Although PMN may not be the only cell type that mediates damage in this circumstance these cells are potential sources of a number of pro-inflammatory molecules. Factors that may blunt inflammation or inhibit cellular release of toxic molecules by PMN would be very useful in reducing tissue injury. However, to date most investigations have been concerned with factors that propagate these reactions rather than attenuate the inflammation.

Indeed, the influx of PMN into pulmonary parenchyma or airways is known to occur through production of numerous agonists that attract cells (Sibille & Reynolds, 1990). Neutrophil activation by peptide agonists such as fMLP, C5a or IL8 occurs through an intricate process that includes plasma membrane receptor binding followed by coupling and activation of associated G proteins (Sklar, 1986). G proteins further activate certain target proteins, some of which mediate phosphorylation of intermediate low molecular weight GTP-binding proteins (Cockcroft, 1989).

There is also evidence that specific tyrosine protein kinases are important in PMN activation through their ability to phosphorylate other target proteins which further transduce the activation signal (Berkow et al., 1989). There is some evidence that coupling of phospholipase D to the chemotactic peptide receptor requires tyrosine phosphorylation while phospholipase C does not have that requirement (Uings et al., 1992). Specific phosphoproteins or protein kinases that are intermediates in the activation cascade for PMN are unclear. Although a ras related protein may be an important intermediate for activation of phospholipase C in other cells this does not appear the case for PMN (Uings et al., 1992).

Several enzymes that cleave phospholipids are involved in cellular activation. Phospholipases $A_2$, C and D are best characterized for their role in PMN activity. Activation of phospholipase c and D occurs following PMN stimulation by coupling of the enzymes to agonist receptors through specific G proteins with subsequent phosphorylation and activation of the enzyme. With activation phospholipase C cleaves between the phosphate and glycero-backbone of membrane phospholipids resulting in production of diacylglycerol and water-soluble inositol derivatives. These byproducts further transduce the signal through further stimulation of intracellular calcium pools, by IP3, and activation of protein kinase C, by diacylglycerol.

More recent studies have examined the role of phospholipase D in neutrophil signal transduction and mechanisms of activation of this enzyme. There is evidence that several factors can activate phospholipase D including calcium and protein kinase C. Recent compelling data suggests calcium activation of a calmodulin dependent protein kinase, presumably myosin light chain kinase, is a major activating factor for phospholipase D (Kanaho et al., 1992). With activation of this phospholipase and production of byproducts the signal is further propagated. There is evidence that part of these effects is to stimulate calcium influx from the extracellular environment.

In the normal lung environment, bronchi are exposed to particulate matter, including bacteria, fungi and dusts, that would be expected to trigger release of molecules that attract PMN. However, as normal bronchi are relatively devoid of PMN, this suggests that there is a mechanism to dampen acute inflammation in the lung. The present inventor reasoned that the identification of molecules which naturally function to inhibit PMN may lead to production of anti-inflammatory agents for use in treating various diseases associated with pulmonary inflammation.

The inventor discovered that normal human bronchial lavage contains a nonpolar peptide capable of inhibiting phagocyte function, such as PMN chemotaxis, oxidant production and degranulation. This inhibitor was demonstrated to be present in bronchoalveolar lavage of normal volunteers in an inverse relationship to the degree of bronchoconstriction and airway inflammation induced by an extract of cotton bracts (Cooper et al., 1991).

The present study was directed to the purification of significant quantities of this inhibitor and to its molecular characterization. The inhibitory material purified from human bronchial lavage was found to comprise two similar peptides, one having eleven amino acids, and a truncated, but otherwise identical peptide of ten amino acids. The amino acid sequence of these peptides is in accordance with the pI and $M_r$ of the natural inhibitor. Peptides with the 11 amino acid sequence Arg-Glu-Gly-Ser-Tyr-Phe-Phe-Gly-Asp-Asn-Ala (seq id no:1) were termed neutrophil inhibitor peptide, NIP, and those with the 10 amino acid sequence Glu-Gly-Ser-Tyr-Phe-Phe-Gly-Asp-Asn-Ala (seq id no:2) were designated NIP-Arg. These sequences were found to be highly homologous to a stretch of amino acids contained in an influenza A nucleoprotein.

A synthetic peptide with a sequence corresponding to that of the native 11-mer peptide was found to inhibit, in a dose-dependent manner, PMN chemotaxis to C5a and fMLP as well as oxidant production in response to fMLP. A synthetic 10 amino acid peptide, which lacked the amino terminal arginine of the 11-mer, was found to be active, but less so than the peptide containing arginine at this position. This suggests that autocatabolism may be a source of decreasing potency.

In addition, the inventor postulates that post-translational modifications may also alter the activity of the natural molecule. The molecule contains a potential phosphorylation site comprising a serine and a tyrosine residue, either or both of which could possibly be phosphorylated. Although it is difficult to assess the degree of phosphorylation in vivo, it appears that the purified peptide that was sequenced was not phosphorylated at these sites because the serine and tyrosine residues produced during the sequencing process co-eluted with the non-phosphorylated forms of the respective amino acids. However, it remains possible that the peptide may have been dephosphorylated during purification. The finding that NIP and related peptides are actively phosphorylated by PMN lysates suggest the natural molecule exists in a non-phosphorylated state and may be phosphorylated as part of its mechanism of action.

Influenza A virus has been shown to deactivate PMN (Hartshorn & Tauber, 1988), although the components of the virus that mediate these effects are currently unknown. In addition to the striking sequence homology, the peptides of the present invention have functional similarities to effects mediated by influenza A viruses. These include the inhibition of PMN chemotaxis, degranulation and oxidant production. Although the subjects who underwent lavage for this study were not rigorously assessed for evidence of a recent infection with influenza, none of them had experienced symptoms of a recent viral infection. In addition, the present inventor has previously demonstrated that human alveolar macrophages produce another similar low $M_r$ inhibitor of PMN function (Sibille et al., 1989). This evidence together suggests that the NIP of the present invention is of human origin.

The mechanisms of PMN deactivation by influenza A virus have been partially characterized. Influenza A virus induces an alteration in protein phosphorylation in response to fMLP (Caldwell et al., 1988) and also alters PMN calcium homeostasis (Hartshorn & Tauber, 1988). As noted, the sequence of NIP disclosed herein contains an apparent phosphorylation site that is consistent with the consensus phosphorylation site specific for calmodulin-dependent protein kinase II (XRXXS/T) (Pearson & Kemp, 1991). Myosin light chain kinase is also a good candidate for effecting phosphorylation as this kinase has been shown to be important in the activation of PMN phospholipase D (Kanaho et al., 1992), an enzyme important for PMN activation.

It is shown herein that PMN lysates actively phosphorylate NIP. In addition, the truncated form of the peptide, GSYFF, was found to inhibit chemotaxis with approximately the same potency of NIP and was also phosphorylated. The inventor proposes that the most likely explanation for inhibition by NIP and related peptides is competitive interaction with a certain protein kinase important for PMN activation. These peptides may compete with larger native substrates for binding to these enzymes but not propagate the activation signal as do the normal substrates.

In addition to inhibiting a number of PMN functions, the peptides of the present invention are proposed to act as a "short circuit" in the signal transduction process, attenuating the normal pathways of phosphorylation that occur with cellular activation. They could therefore prove be useful models for investigating certain signal transduction and phosphorylation pathways that operate within PMN and other phagocytic cells.

The cause of NIP's lability when incubated with PMN is not clear. One possibility is that the molecule may become phosphorylated through competition with a signal molecule for a PMN protein kinase and, after phosphorylation, no longer competes. If this is the case, then peptides that interact with the same kinase but do not become phosphorylated may be more potent than NIP. Alternatively, PMN proteases may degrade the molecule into inactive fragments. The present inventor has previously shown that aminopeptidase, an enzyme present in PMN, degrades natural bronchial lavage-derived PMN inhibitor.

The peptide inhibitors of the present invention are proposed to be physiologically important anti-inflammatory modulators in humans. NIP or an NIP-like peptide may, further, have been incorporated into the influenza virus genome at some point in the distant past. Although current data suggest synthetic NIP is ultimately deactivated by PMN, the present inventor has contemplated various peptide manipulations, such as amino acid substitutions, to protect this molecule from deactivation. Thus NIP itself, and second generation NIP analogues, are proposed to be ideal candidates for use as powerful anti-inflammatory agents in the treatment of, for example, rheumatoid arthritis, inflammatory bowel disease, reperfusion cardiac damage, and particularly, asthma and chronic bronchitis.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

PURIFICATION OF CHEMOTAXIS-INHIBITING PEPTIDES

1. Bronchoalveolar Lavage and PMN Isolation

To obtain sufficient inhibitor peptide for analysis bronchoalveolar lavage was performed on lungs obtained from heart transplant donors. At the time of death there was no evidence of lung infection or any history of previous lung disease. Bronchoalveolar lavage was performed by cannulating a subsegmental orifice with a catheter, occluding the airway around the catheter with a suture, lavaging the distal airways with a total of one liter of Hanks balanced salt solution without calcium or magnesium (MHS) and retrieving eluant by gentle suction. The lavage fluid was immediately placed on ice and cells were separated from supernatant by centrifugation (400×g for 15 minutes). Cell-free supernatant was then frozen at −80° C. until fractionation.

Whole blood was obtained from a normal human volunteer population and PMN were isolated by ficoll-hypaque gradient centrifugation followed dextran sedimentation, as described by Cooper et al., (1991).

2. Purification of Inhibitory Peptides

Inhibitor peptide was purified from one liter of lavage fluid using an initial preparation with C18 cartridges (Baker), followed by preparative isoelectric focusing and reverse phase high performance liquid chromatography (RPHPLC). 20×6 ml C18 cartridges were first prepared with methanol and water and one liter of lavage was loaded into the cartridges at 50 ml of lavage fluid per cartridge. Cartridges were then washed with 20 ml of double distilled water that had been filtered through a 2 μm filter. Following an air purge of 10 ml, nonpolar material was eluted with 9 ml of methanol. The eluted material was evaporated (Savant) to a volume of approximately 5 ml and was then subjected to preparative isoelectric focusing.

Following preparative isoelectric focusing using 8 different preparations of C18-fractionated bronchoalveolar lavage material, the material with inhibitory activity was found to have a pI of 4.5 (FIG. 1). Accordingly, for the large scale preparation of the inhibitor, the C18-eluted material was loaded onto a preparative isoelectric focusing apparatus (Rotofor, Biorad) that had been prefocused for one hour with ampholytes (Biolytes, Biorad) that generated a pH gradient ranging from 4–6. The loaded material was then focused for an additional 2 hours and fractions were retrieved by aspiration as directed in the apparatus instructions. This range of ampholytes and length of focusing was determined by previous runs using ampholytes that generated a wider pH gradient range and by varying the amount of focusing time.

The pH of each of the fractions were determined and fractions at pH 4.0–5.0 were loaded onto C18 cartridges and eluted with methanol. This material was evaporated and rediluted in 500 μl of 0.1% trifluoroacetic acid (TFA). Undissolved material was then removed by centrifugation and the entire sample was subjected to reverse phase HPLC using a semipreparative C18 column (Rainin) connected to an HPLC system with dual pumps (Rainin). Material from the column as eluted at 4 ml/min using a linear gradient of 0.1% TFA to 70% acetonitrile/0.085% TFA over 45 minutes then held at this latter buffer for an additional 10 minutes. Absorbance was monitored at 280 nm and one minute (4 ml) fractions were collected.

Figure 2:
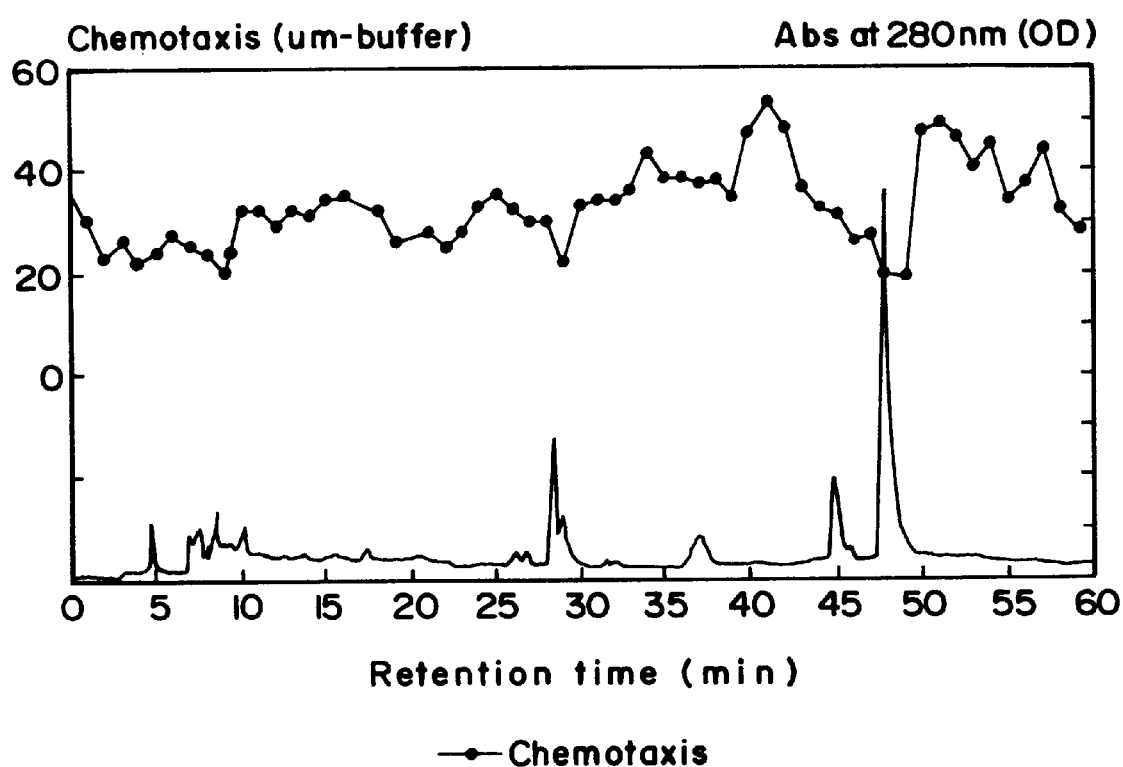
FIG. 2. Chromatogram of fractionated bronchoalveolar lavage. Bronchoalveolar lavage was fractionated using C18 cartridges, isoelectric focusing then C18 cartridges again and injected into a semipreparative C18 column and eluted with a TFA/acetonitrile gradient mobile phase at a flow of 4 ml/min as outlined in Example I. One minute fractions were collected and diluted 1:1000 into 10 $\mu$M C5a. Chemotactic activity (top tracing) was assessed as in FIG. 1. The bottom tracing shows absorbance at 280 nm.
Figure 3:
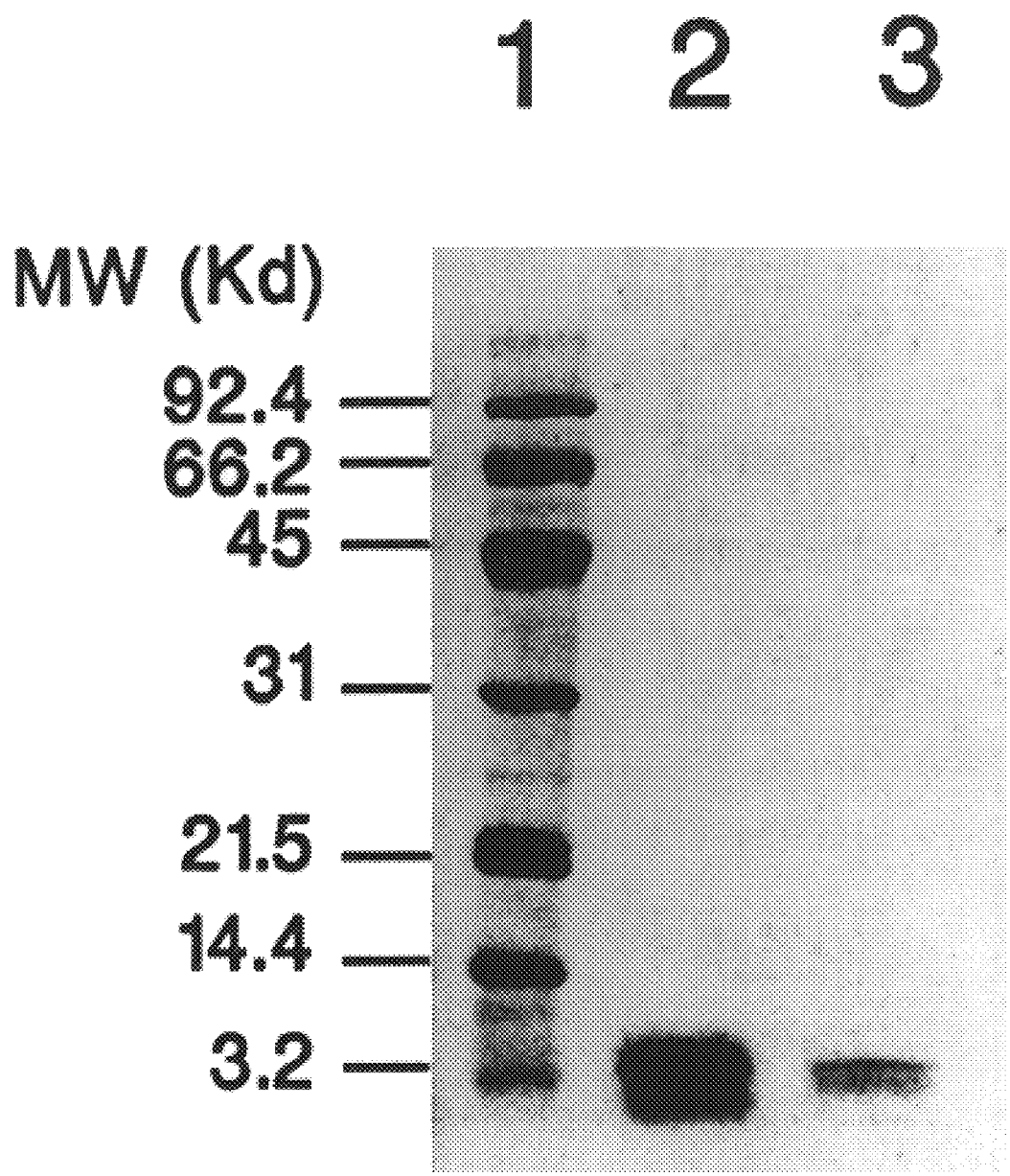
FIG. 3. SDS polyacrylamide gel electrophoresis (SDS/PAGE) of purified fractions containing neutrophil inhibitor peptide (NIP) and the NIP-Arg peptide. The purified fractions, eluted at 46–50 minutes from the C18 column during the final purification step described in FIG. 2, were concentrated and run on a 12% SDS polyacrylamide gel. Lane 1, low $M_r$ standards; lane 2,. vasoactive intestinal polypeptide ($M_r$ 3.2 kd); lane 3, purified fractions of NIP and NIP-Arg.

Several fractions from the semipreparative HPLC C18 column elution inhibited PMN chemotaxis to human recombinant C5a, however, the major peak of inhibitory activity was found to elute at 46–48 minutes (FIG. 2). Subsequently the 46–48 minute fractions were pooled, evaporated and resuspended in buffer, boiled and subjected to SDS\PAGE on a 12% gel. This purified preparation exhibited a single band of protein migrating with a very low $M_r$ standard (FIG. 3).

EXAMPLE II

CHARACTERIZATION OF NIP AND NIP-ARG

1. Amino Acid Sequence Analysis

The inhibitor material purified from bronchoalveolar lavage was subjected to amino acid sequencing using an Applied Biosystems peptide sequencer housed in the UAB protein analysis core facility. Such sequence analysis of this purified material revealed two peptides (Table 1) with identical sequences except for the addition of an arginine at the amino terminal site in one peptide. The serine and tyrosine residues detected during the sequencing process co-eluted with non-phosphorylated forms of the respective amino acids. This suggests that the peptide purified from its natural environment was not phosphorylated at these sites. However, the process involved in purification of the peptide might have resulted in peptide dephosphorylation.

The peptide sequences exhibited striking homology to a stretch of amino acids in the sequence of a nucleoprotain produced by certain influenza A viruses (seq id no:16; Table 1). Partial homology to sequences within myf-6, ros and neu oncogene-related proteins was also observed. For example, the sequence GSYFF occurs in the Myf-6 oncogene-related protein, one function of which appears to be in muscle development (Bober et al., 1991).

TABLE 1

Sequence of inhibitor peptides and relevant portion of Influenza A nucleoprotein

| | |
|---|---|
| Peptide 1: (corresponds to seq id no:1) | Arg-Glu-Gly-Ser-Tyr-Phe-Phe-Gly-Asp-Asn-Ala |
| Peptide 2: (corresponds to seq id no:2) | Glu-Gly-Ser-Tyr-Phe-Phe-Gly-Asp-Asn-Ala |
| Nucleoprotein: (seq id no:16) | Asn-Glu-Gly-Ser-Tyr-Phe-Phe-Gly-Asp-Asn-Ala- (482)                                                            (490) |

2. Synthetic Peptides

Two synthetic peptides, with sequences which correspond to the sequences of the natural inhibitory peptides, were initially produced in the UAB protein analysis core facility on a Biosystems Peptide synthesizer. The accuracy of synthesis was determined by analysis of amino acid composition. Purification of synthetic peptides was performed by RPHPLC using the column and mobile phase employed for the purification of the native peptides, as described above, and purification was verified by SDS-PAGE. Protein concentrations were determined using a microplate colorimetric method employing coomassie blue as a substrate. The endotoxin content of diluted synthetic peptides, as determined by the limulus lysate test (Associates of Cape Cod, Inc., Woods Hole, Mass.; Cooper et al., 1986; sensitivity, 4.0 pg/ml) was <40 pg/ml (<800 pg/mg peptide) in all instances.

The 11 amino acid synthetic peptide (Peptide 1 in Table 1) was termed neutrophil inhibitor peptide, NIP, (seq id no:1), and the 10 amino acid synthetic peptide (Peptide 2 in Table 1) was designated NIP-Arg (seq id no:2). In addition, a peptide with the same proportion of amino acids as NIP but in a random sequence (SNRGFAYFDEG, seq id no:21) was produced for use as a control in cellular function studies.

As the sequence of NIP includes an apparent phosphorylation site, a truncated peptide, GSYFF (seq id no:3), containing this phosphorylation sequence was also produced. During this study, the idea that NIP and NIP-like peptides and derivatives may be phosphorylated as part of their mechanism of action and that such phosphorylation may result in the reduction of their inhibitory actions was formulated by the inventor. Therefore, a range of second generation peptides with sequences based upon GSYFF, but containing modifications in the phosphorylation site, were designed. To date, three of such peptides, namely Gly-Ala-Ala-Phe-Phe (seq id no:12), Gly-Ser-Ala-Phe-Phe (seq id no:13) and Gly-Ala-Tyr-Phe-Phe (seq id no:14) have been synthesized.

3. Effects of Synthetic Peptides on PMN Chemotaxis

The degree of inhibition of PMN chemotaxis by natural purified inhibitor or synthetic peptides was determined as described by cooper et al. (1991) using 100 nM formyl-methionyl-leucyl-phenylalanine (fMLP), 10 nM human recombinant C5a or 10 nM leukotriene $B_4$ and multiwell chemotaxis chambers (Neuroprobe Inc., Bethesda, Md.) employing nitrocellulose membranes. Isoelectric focused fractions or HPLC elution fractions were diluted 1:1000 in a final concentration of the above agonists. Controls included buffer alone or C5a diluted in buffer alone. Sham HPLC injections were also used to establish that mobile phase or focused fractions diluted in a similar manner did not affect PMN chemotaxis.

22 µl of samples were placed in bottom wells of the chemotaxis chamber, a nitrocellulose membrane with 3 µm pores was overlaid as was a rubber gasket. The top plate of the chamber was then secured and the entire chamber was warmed to 37° C0 for 15 minutes. 50 µl of PMN suspended at $1.5 \times 10^6$/ml in HBSS with 0.1% BSA were then added to the top wells and the plates were incubated for an additional 1–1½ hours. Chemotaxis was assessed by comparing the maximal distance migrated to agonist alone or in the presence of an irrelevant peptide (µm minus migration to buffer alone) and comparing to the distance migrated to agonist plus elution fractions or synthetic peptides. The percentage of total cells migrating 10 µm increments from 0 to 120 µm was also determined by image analysis (Olympus Instruments) and treatment groups were compared to controls. Synthetic peptides were also incubated with PMN for varying amounts of time, then PMN were assessed for chemotaxis to recombinant C5a.

Figure 4A:
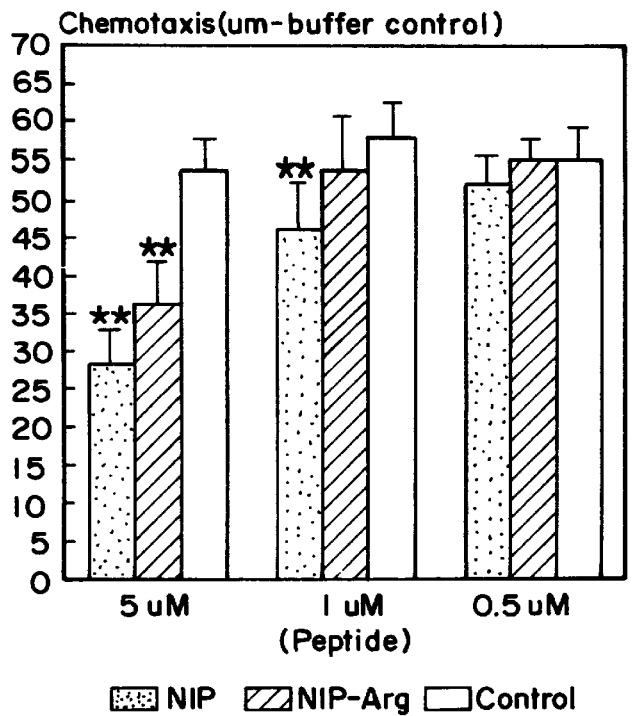
FIG. 4. Effects of synthetic NIP (black bars), NIP minus the amino terminal arginine, NIP-Arg, (gray hatched bars) and control peptide (stippled bars) on polymorphonuclear neutrophil (PMN) chemotaxis to 10 nM human recombinant C5a (A) and 100 nM fMLP (B). Chemotaxis is expressed as in FIG. 1. Peptides were diluted at final concentrations noted into agonist so that PMN were exposed to agonist and peptides at the same time (** $p<0.01$ vs control peptide; * $p<0.05$ vs control peptide).
Figure 4B:
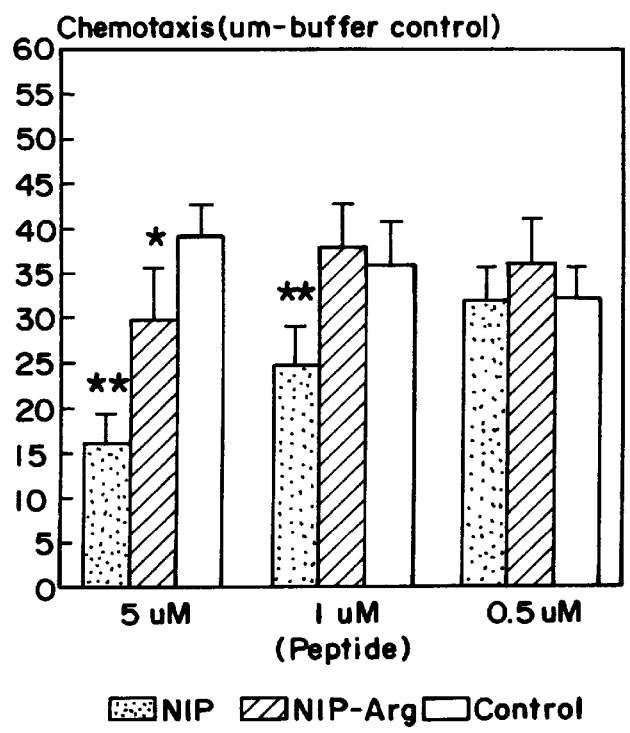
Figure 5:
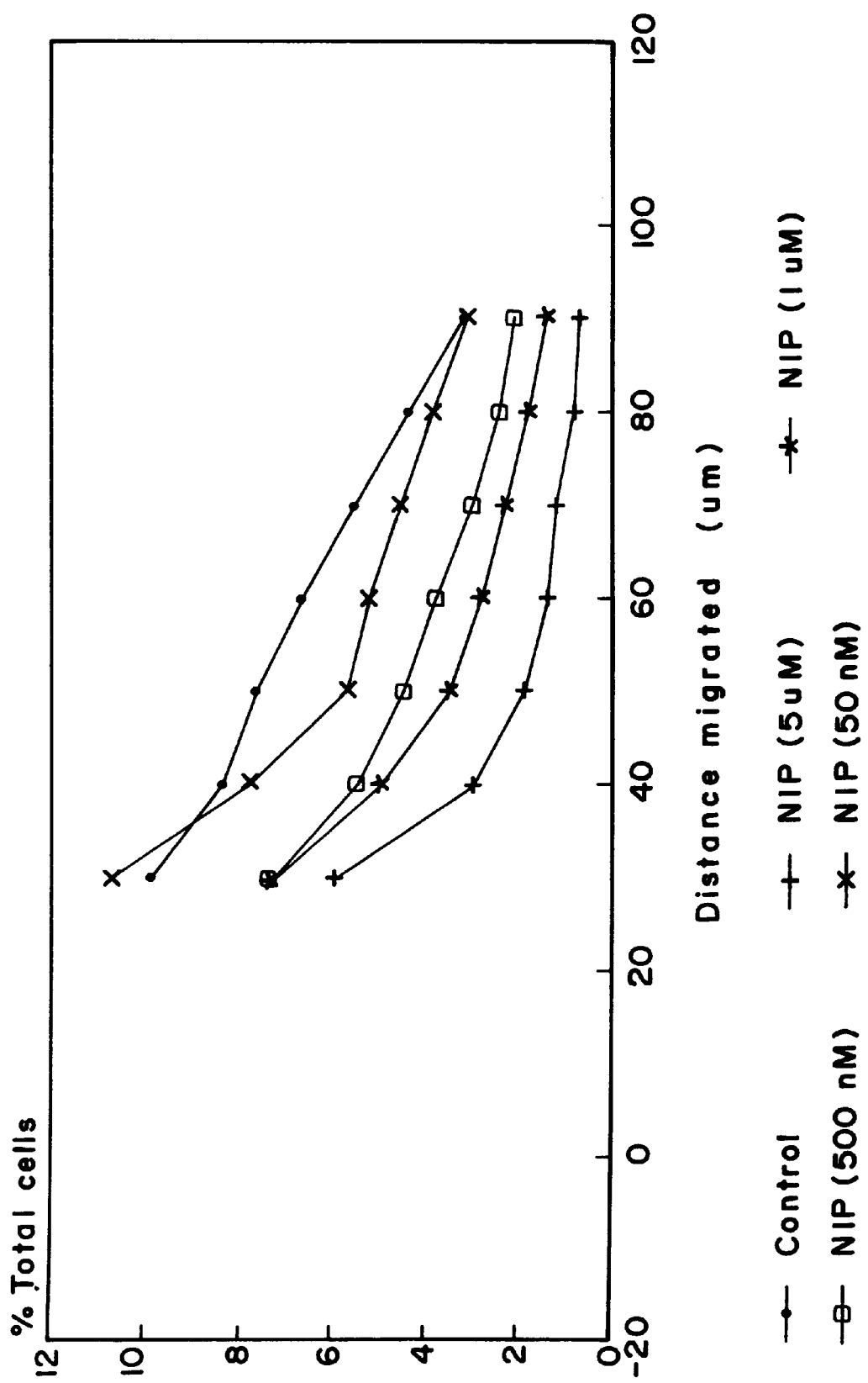
FIG. 5. The percentage of total PMN migrating to 10 nM C5a in the presence of varying concentrations of NIP or 5 $\mu$M control peptide. Each point represents the mean of four determinations performed on separate days, standard deviations varied less than 10% (** $p<0.01$ vs control peptide).

Using this assay, it was found that synthetic NIP (seq id no:1) inhibited PMN chemotaxis to C5a and fMLP when cells were concomitantly exposed to NIP and agonist (FIG. 4). NIP without arginine in the amino terminal position, NIP-Arg (seq id no:2), also significantly inhibited PMN chemotaxis but with a slightly higher $IC_{50}$ (6 µM) than NIP containing arginine ($IC_{50}$=2 µM) for C5a-induced chemotaxis. When chemotaxis was assessed by counting the number of cells migrating 10 µm increments a dose-dependent inhibition of chemotaxis to C5a was once again noted (FIG. 5).

Figure 6:
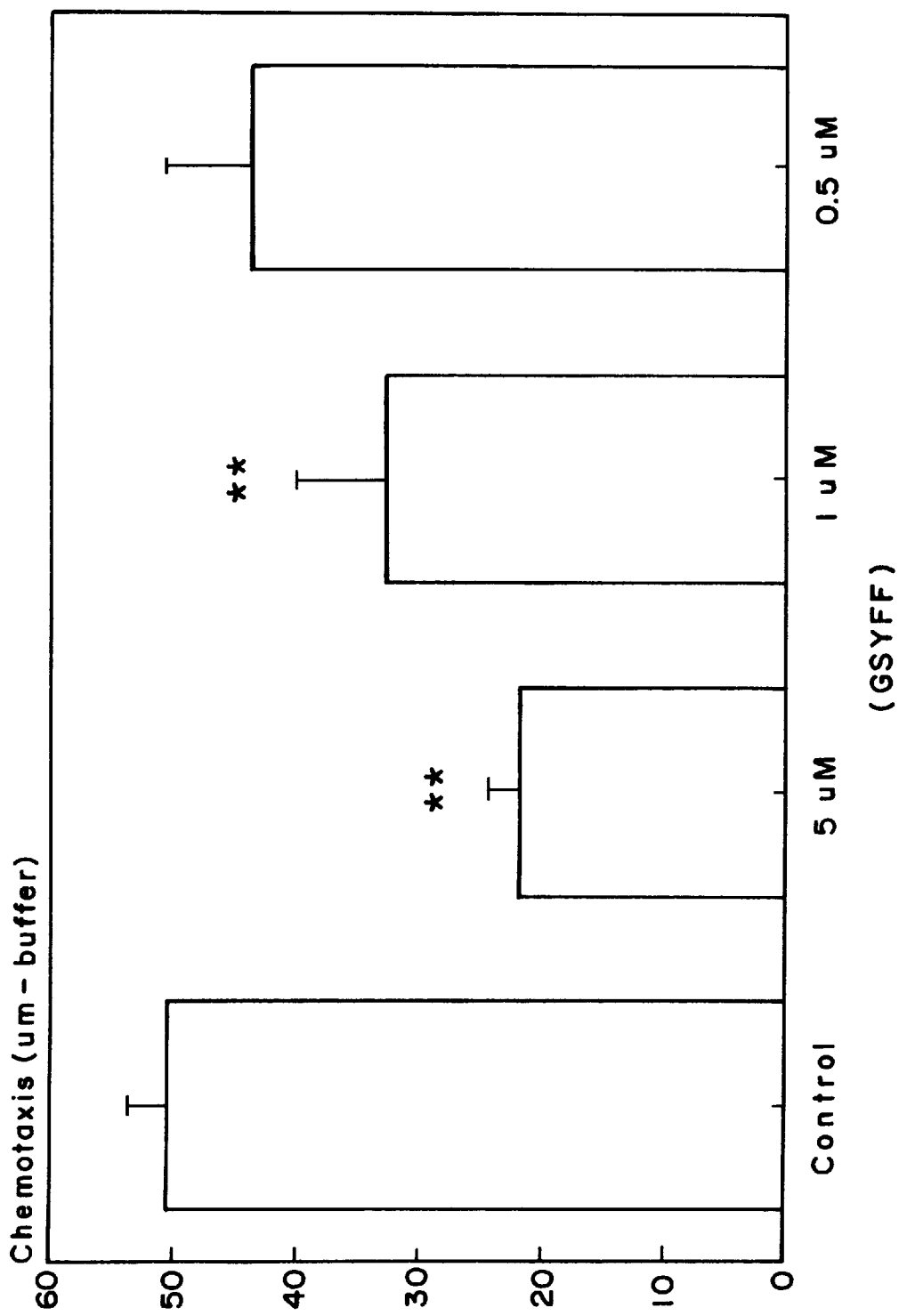
FIG. 6. Effects of synthetic peptide GSYFF on PMN chemotaxis to recombinant C5a. Chemotaxis is expressed as in FIG. 4 (** $p<0.01$ vs control).

A truncated peptide with the sequence GSYFF (seq id no:3) also significantly inhibited PMN chemotaxis to recombinant C5a, with approximately the same potency as NIP, when agonist and peptide were exposed to cells at the same time (FIG. 6).

As trace levels of endotoxin concentrations may inhibit PMN chemotaxis (Haslett et al., 1985), the possible contribution of endotoxin to PMN inhibition in the present study was considered. However, two pieces of information indicate that endotoxin is not an active component of natural or synthetic NIP. First, both natural and synthetic NIP inhibit fMLP-stimulated PMN superoxide production, while endotoxin has been shown to "prime" PMN to produce more superoxide on stimulation with fMLP. Second, using the limulus lysate assay, it was shown that preparations of natural and synthetic NIP that inhibit PMN chemotaxis are not contaminated with detectable (<500 pg/ml) endotoxin.

4. Effect of Synthetic Peptides on PMN Superoxide Production

PMN superoxide production in the presence of synthetic peptides was measured using an assay utilizing the reduction of ferricytochrome C by superoxide, as described by Cooper et al. (1988). PMN were suspended at $4 \times 10^6$/ml in HBSS, and 50 µl of cells were added to wells in a 96 well microtiter plate (Dynatech). 10 µl of the test or control (irrelevant) synthetic 15 peptides were then added and the mixtures were incubated at room temperature for varying amounts of time.

50 µl of HBSS or superoxide dismutase (12.5 µg/ml final concentration; Sigma biochemicals) were placed in appropriate wells, cytochrome C (80 µM final concentration) was then added, followed by fMLP (10 µM final concentration). Plates were incubated for one hour at 37° C. and absorbance was determined at 550 nm on a microplate reader (Dynatech).

Figure 7:
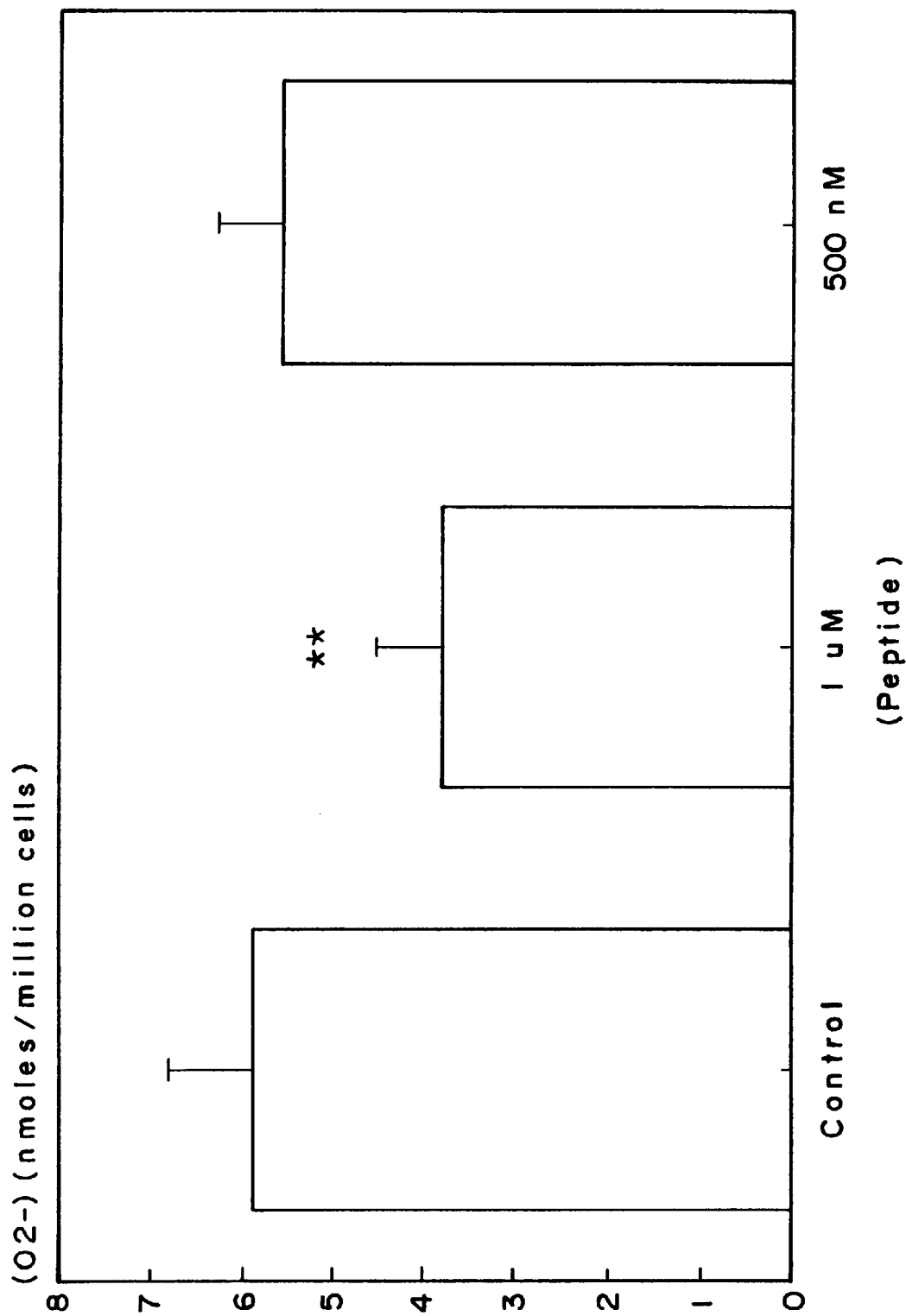
FIG. 7. Effect of pre-exposure of PMN to NIP on superoxide production in response to 10 $\mu$M fMLP. PMN were exposed to NIP or control peptide for 15 minutes at room temperature prior to addition of fMLP and superoxide production was determined after incubation at 37° C. for one hour (** $p<0.01$ vs control peptide).

It was determined that PMN exposed to 1 µM NIP (seq id no:1) 25 for 15 minutes prior to addition of fMLP produced significantly less superoxide than control PMN (FIG. 7). This was not due to nonspecific effects of NIP as addition of the peptide after cells were stimulated with fMLP for 60 minutes did not affect cytochrome C reduction.

Preliminary data was also obtained to show that the 10 amino acid synthetic peptide NIP-Arg (seq id no:2) and the truncated peptide GSYFF (seq id no:3) also inhibit fMLP-stimulated PMN superoxide production.

5. Kinetics of Inhibition by Synthetic Peptides

Figure 8A:
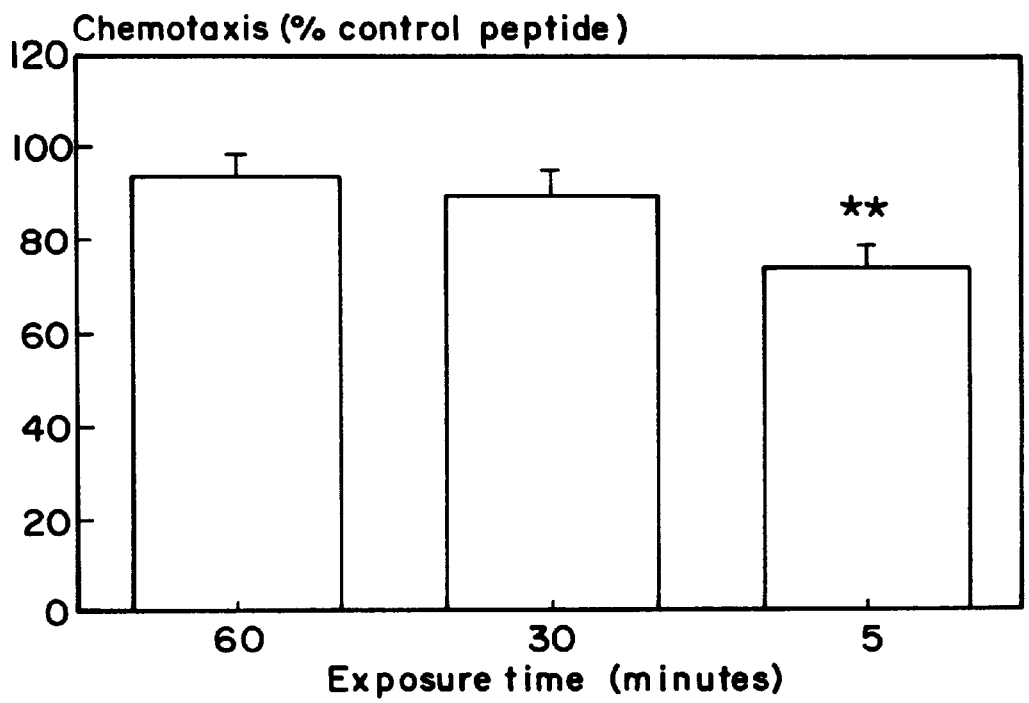
FIG. 8. Kinetics of inhibition of chemotaxis to C5a (A) and fMLP-induced superoxide production (B) by 5 $\mu$M NIP. Cells were preexposed to NIP for varying amounts of time or 5 $\mu$M control peptide (abscissa) at room temperature. Cells were then added to chambers and chemotaxis to C5a was assessed after an additional 75 minutes of incubation at 37° C. Superoxide production was assessed 60 minutes after addition of fMLP at 37° C. (** $p<0.05$ vs control peptide).
Figure 8B:
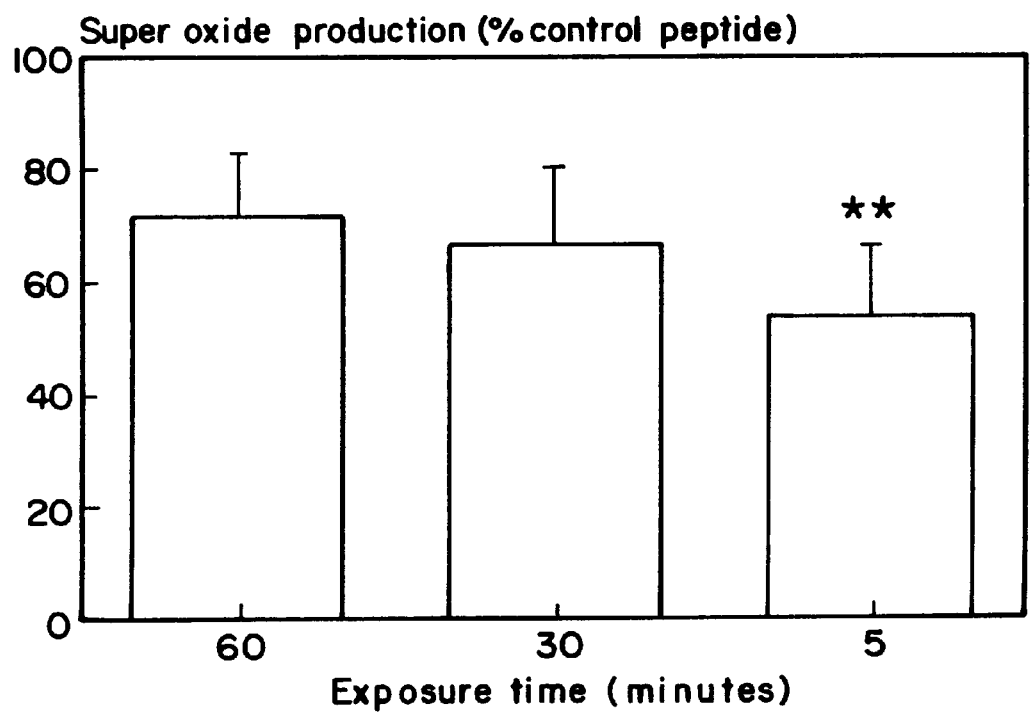

When PMN were exposed to synthetic NIP (seq id no:1) for varying amounts of time inhibition of both C5a induced chemotaxis (FIG. 8a) and fMLP-induced superoxide release (FIG. 8b) was noted within 5 minutes of exposure. However, the magnitude of chemotaxis or superoxide inhibition by NIP diminished with increased exposure time, such that at 60 minutes the inhibition was no longer apparent.

6. Phosphorylation of Synthetic Peptides by PMN Lysates

Whole PMN lysates were obtained by rocking $100 \times 10^6$ PMN for 20 minutes at 4° C. in 4 ml of a tris lysis buffer containing 1% triton, PMSF and aprotinin. After incubation, lysis was confirmed by light microscopy, the debris was removed by centrifugation at 10000 g for 20 minutes and the supernatant was removed and frozen prior to use.

On the day of the assay 400 µl of these lysates were combined with 40 µg of synthetic NIP (seq id no:1), NIP-Arg (seq id no:2), GSYFF (seq id no:3), or buffer alone, in the presence of 40 µCi [$\gamma$-$^{32}$P]ATP in phosphate-poor RPMI containing $MgCl_2$ and $MnCl_2$. As controls, synthetic peptides were also incubated with [$\gamma^{32}$P]ATP in the absence of PMN lysates, or in the presence of lysates from U937 (irrelevant) cells. The mixtures were incubated at room temperature for one hour then 45% formic acid and 25 mM ATP were added to stop the reaction and the suspensions were loaded onto C18 sep pak cartridges and eluted with methanol. Methanol eluates were evaporated, resuspended in SDS sample buffer and run over 15% SDS-PAGE. The gel was stained with coomassie brilliant blue, dried, and subjected to autoradiography. Certain suspensions were also injected into the semipreparative C18 column and eluted with the mobile phase, as described above. One minute (4 ml) fractions were collected and 500 µl aliquots were assessed for $^{32}$P incorporation by scintillation counting.

Figure 9:
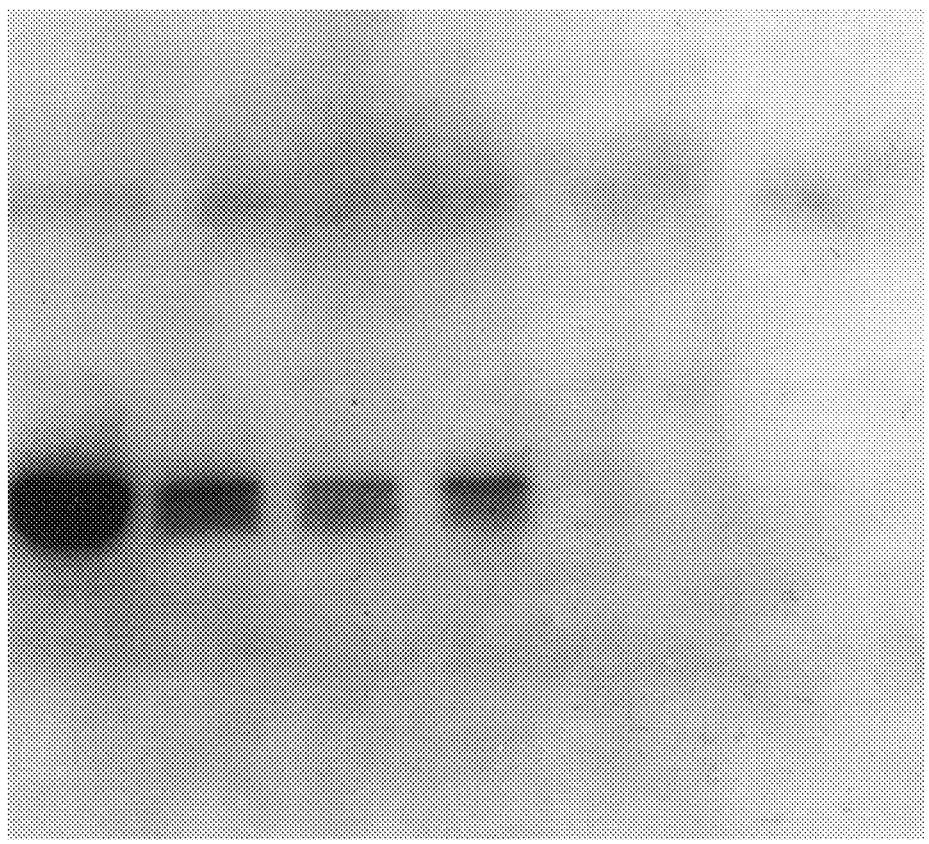
FIG. 9. Autoradiogram of NIP (lane A), NIP-Arg (lane B), GSYFF (lane C) or control peptide (lane D) exposed to PMN lysates in the presence of [$\gamma$-$^{32}$P]ATP. Lanes E-F contain NIP, NIP-Arg, GSYFF exposed to [$\gamma$-$^{32}$P]ATP in the absence of PMN lysates.
Figure 10:
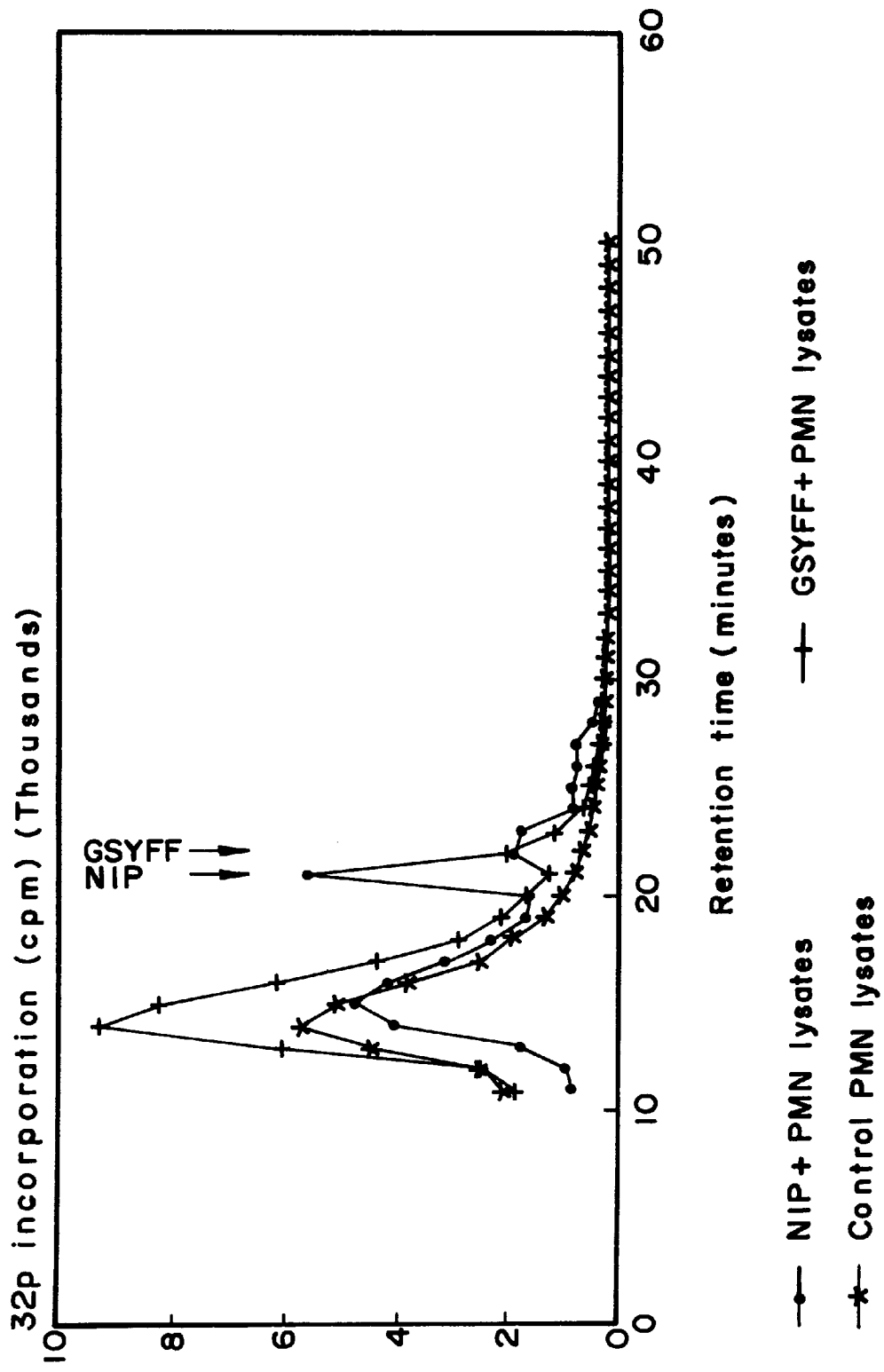
FIG. 10. Chromatogram of material from NIP, GSYFF or control exposed to PMN lysates in the presence of [$\gamma$-$^{32}$P] ATP and injected into RPHPLC using the mobile phase. 4 ml fractions were collected and $^{32}$P incorporation was assessed by scintillation counting of 500 $\mu$l. Elution times of NIP and GSYFF are noted.

FIG. 9 shows an autoradiogram of synthetic peptides exposed to [$\gamma$-$^{32}$P]ATP and PMN lysates. Exposure of NIP (seq id no:1) to PMN lysates, but not U937 lysates, under these conditions resulted in intense incorporation of $^{32}$P, indicating that PMN-specific phosphorylation was occurring. Phosphorylation of NIP-Arg (seq id no:2) also noted under these conditions but to a lesser degrees. In addition, although phosphorylation of GSYFF (seq id no:3) was not readily apparent from the autoradiogram, when the suspension containing this peptide was injected into RPHPLC using the mobile phase previously described, a peak of phosphorylation, absent in the control injection, co-eluted with GSYFF (FIG. 10).

Figure 11A:
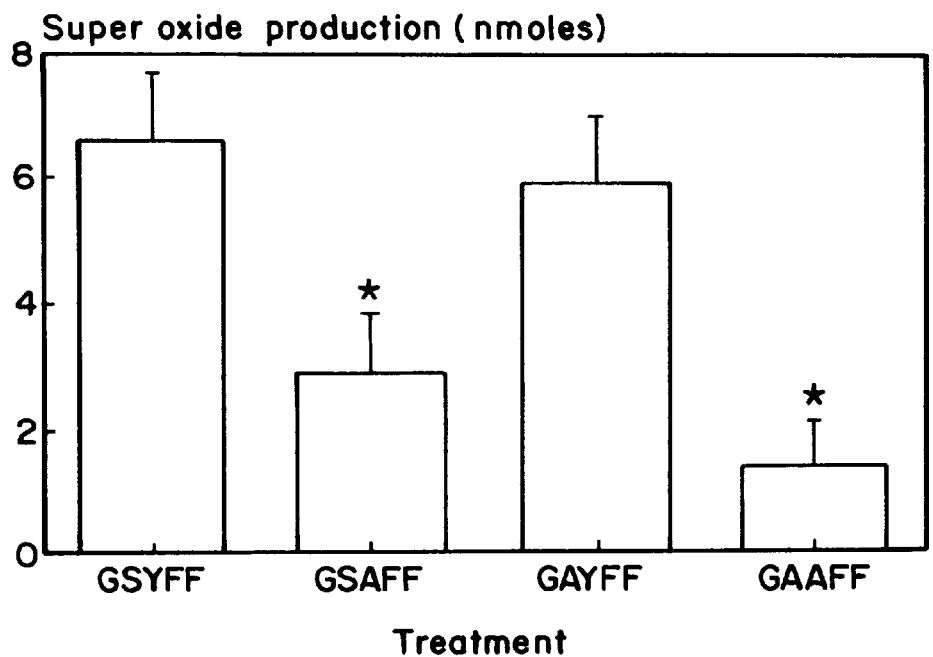
FIG. 11. The effects of modified pentapeptides on C5a-induced chemotaxis (A) and fMLP-induced superoxide production (B) by PMN. PMN were incubated with the indicated peptides for 15 minutes prior to performance of the assays, as described above. (** $p<0.05$ vs Gly-Ser-Tyr-Phe-Phe)
Figure 11B:
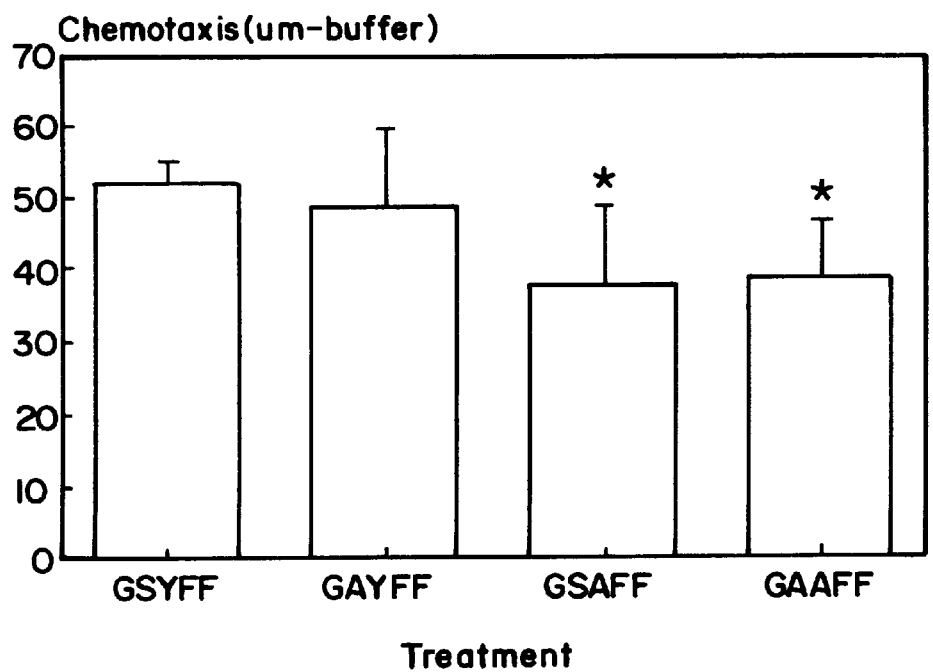

More recent studies have shown that site mutagenesis of the phosphorylation site of the Gly-Ser-Tyr-Phe-Phe (seq id no:3) peptide results in dissociation of the effects on chemotaxis and superoxide production as well as more stability in the effects. Treatment of PMN with either Gly-Ser-Ala-Phe-Phe (seq id no:13) or Gly-Ala-Ala-Phe-Phe (seq id no:12) markedly attenuated fMLP-induced superoxide production (FIG. 11a) in comparison to Gly-Ala-Tyr-Phe-Phe (seq id no:14). In contrast, Gly-Ala-Tyr-Phe-Phe (seq id no:14) more significantly inhibited chemotaxis to C5a when compared to Gly-Ser-Tyr-Phe-Phe (seq id no:3) or the other peptides (FIG. 11b).

7. Assessment of Cellular Viability

PMN viability after exposure to NIP (seq id no:1) or control peptide for varying amounts of time was assessed by measuring LDH release using a commercially available kit (Sigma). It was found that exposure of PMN to concentrations of NIP that inhibited chemotaxis and oxidant production did not significantly alter cellular viability, as determined by LDH release (Table 2).

TABLE 2

LDH concentrations of supernatant after exposure to NIP

| Exposure | Concentration ($\mu$M) | Duration (min) | [LDH] |
| --- | --- | --- | --- |
| HBSS | — | 60 | 37.5 ± 5.5 |
| Triton | 0.1% | 5 | 252 ± 6.5 |
| Control peptide | 5 | 60 | 39.2 ± 6.5 |
| NIP | 5 | 60 | 35 ± 5.5 |
| NIP | 5 | 30 | 30.2 ± 4.25 |
| NIP | 5 | 15 | 40.8 ± 3.7 |
| NIP | 5 | 5 | 37.2 ± 6.3 |

8. Effect of NIP Inhibitory Material on PMN Elastase Release

In contrast to the results documented above, the inhibitor peptides employed in the following studies (sections 8 through 13) were not synthetic peptides. The material used for each of the subsequently described bioassays was purified from natural sources by Sep-pak and RP-HPLC and the inhibitors fractions were identified. All preparations of inhibitor were free of detectable (<1 pg/ml) lipopolysaccharide as assessed by the limulus lysate test. PMN preincubated with inhibitor purified by RP-HPLC showed diminished release of elastase when stimulated with 1 $\mu$M fMLP.

9. Effect of NIP Inhibitory Material on PMN Cytosolic Calcium Concentrations

Indo-loaded PMN exposed to RP-HPLC fractions that inhibited chemotaxis and superoxide production displayed an increase in cytosolic calcium concentration. The rise in cytosolic calcium concentrations occurred within 15 seconds of exposure to the fractions and was also apparent if PMN were exposed to fractions in the absence of extracellular calcium. The rise was not reproduced by addition of RP-HPLC elution fraction to indo 1AM in the absence of cells and did not occur if elution fraction from a sham injection was added.

10. Effect of NIP Inhibitory Material on PMN Calcium Transients Induced by fMLP

RP-HPLC elution fractions that inhibited PMN chemotaxis and oxidant production attenuated fMLP-induced increases in cytosolic calcium concentrations if PMN were exposed in the presence of extracellular calcium. However, if extracellular calcium was absent no significant effect on fMLP-induced rise in cytosolic calcium by the inhibitor was noted.

11. Effect of Pertussis Toxin Pretreatment on Calcium Transients

Pretreatment of indo-loaded PMN with pertussis toxin significantly attenuated the increases in cytosolic calcium concentrations mediated by inhibitor fractions. Attenuation of the rise in cytosolic calcium concentration induced by 1 $\mu$M FMLP was also noted, but there was no effect of pertussis toxin on ionomycin-induced rise in cytosolic calcium.

12. Effect of Calcium Transient Buffering on Inhibition of PMN Chemotaxis

To determine if calcium transients were important for PMN inhibition by RP-HPLC elution fractions, PMN were loaded with 10 $\mu$M Quin 2 AM or exposed to TMB-8. This concentration of Quin significantly buffered rises in cytosolic calcium concentrations as evidenced by the return of fluorescence to baseline within one minute after 1 $\mu$M fMLP stimulation in Quin-loaded PMN, in comparison to >10 minutes in Indo-loaded PMN. Inhibition of PMN chemotaxis to human recombinant C5a by RP-HPLC elution fractions was attenuated in PMN loaded with Quin 2AM or exposed to TMB-8.

13. Effect of NIP Inhibitory Material on PMN Chemotactic Peptide Binding

Exposure to inhibitor fractions at 4° C did not significantly affect PMN binding of $^3$H-fMLP. However, increased $^3$H-fMLP binding was noted in PMN exposed to inhibitor for 15 minutes at room temperature followed by $^3$H-fMLP for 15 minutes at 37° C. This enhancement of binding was attenuated by pretreatment with TMB-8. The degree of binding enhancement correlated with the relative amount of inhibitory activity and the propensity to increase PMN cytosolic calcium concentrations in individual preparations. When PMN were exposed to inhibitor for 15 minutes followed by addition of $^3$H-fMLP for 10 minutes, all at 37° C., there was a significant reduction in available plasma membrane chemotactic peptide binding sites suggesting the previously noted enhancement of fMLP binding preceded internalization of receptors.

EXAMPLE III

FURTHER CHARACTERIZATION OF NIP

This example is directed to the techniques contemplated by the inventor for use in the further characterization of NIP and in further defining its mode of action.

1. Action on other Cell Types

In addition to its effects on PMN, the inventor considers it likely that NIP will exert an inhibitory effect on other cells, such as macrophages, eosinophils and monocytes. This may be investigated using a variety of different techniques, as described above for PMN, but substituting the cell type in the various bioassays. Other cells, such as monocytes, may be harvested by cell separation, for example, on an IBM cell separator using accepted techniques.

2. Phosphorylation of NIP

To determine whether NIP is phosphorylated by intact PMN, one would pre-load intact cells with $^{32}$P and conduct labelling studies. For example, PMN cells may be labelled with 1 mCi/ml [$^{32}$P]orthophosphate for 1–2 hours and then exposed to concentrations of NIP that inhibit chemotaxis. The incorporation of phosphate could then be assessed by autoradiography of SDS/PAGE gels. Specific phosphoamino acids of phosphorylated NIP may be quantitated by HPLC (Ringer, 1991) or by thin layer chromatography (Franklin et al., 1991).

3. Effects of NIP on PMN Kinase-Mediated Phosphorylation

There is some previous evidence that influenza A mediates inhibition of PMN activation through effects on cellular protein phosphorylation (Caldwell, et al., 1988). The present inventor postulates that similar effects may occur through exposure to NIP. The effects of the inhibitor, with or without FMLP stimulation, on PMN protein phosphorylation may be determined, for example, using single or two dimensional electrophoresis and indirect autoradiography (Franklin et al., 1991).

4. Identification of Kinases which Phosphorylate NIP

Two approaches are contemplated by the present inventor to be particularly useful for this study. As PMN lysates are known to phosphorylate NIP in the presence of calcium and ATP, one approach will be to purify the specific kinase(s) from PMN lysates. Another useful approach would be to analyze a battery of purified protein kinases including protein kinase C, myosin light chain kinase or other calmodulin-dependent kinases, such as those obtained from commercial sources or purified by natural or recombinant means. One would incubate NIP with the candidate kinase(s) or cellular extracts and the appropriate cofactors in the presence of $^{32}$p-ATP. A peptide containing the same proportion of amino acids but in a different sequence from NIP, such as Ser-Asn-Arg-Gly-Phe-Ala-Tyr-Phe-Asp-Glu-Gly (seq id no:21), is proposed to be a useful control in studies such as these.

5. Phospholipase C and D Activity

Breakdown of phosphoinositol by membrane bound polyphosphoinositide phosphodiesterase precedes cellular cytosolic calcium changes and cellular oxidant production or chemotaxis. Phospholipase C activation with production of $IP_3$ is believed to be important in the production of intracellular calcium shifts, whereas phospholipase D activation with production of phosphatidylethanol appears to trigger influx of calcium from the extracellular compartment. The present inventor hypothesizes that NIP activates phospholipase C but does not allow propagation of the signal to activation of phospholipase D. To investigate this, the effects of the inhibitor on cellular $IP_3$ and $IP_2$ generation will be examined (Rossi et al., 1986).

To conduct such studies the following protocol is proposed. PMN should be washed in buffer, then resuspended to 190–250×10$^6$/ml and labelled with 20 uCi/ml $^3$H-myoinositol for 2 hours at 37° C., washed twice and resuspended to 100×10$^6$ cells/ml. About 900 μl of cells should be incubated in test tubes, in the presence or absence of PMN inhibitor, at 37° C. for about 15 minutes, then exposed to 1 μM FMLP, or buffer alone, for about 20 seconds. The reaction should be terminated with an equal volume of 15% TCA at 4° C. and the precipitate may be removed by centrifugation. Supernatants should be vortexed for 60 seconds with 3 ml of ether and the aqueous phase retained for centrifugation. This procedure should be repeated twice and the aqueous supernatant is kept at 4° C. overnight, with pH adjusted to pH 7 with sodium tetraborate if necessary.

Supernatants obtained in this manner should then be applied to disposable columns of anion exchange resin (BioRad) and sequential elution of inositol phosphates may be achieved using water for 6 minutes, then a gradient of water progressing to 100% IM ammonium formate (pH 3.7) over 24 minutes, then 100% ammonium formate for 5 minutes followed by a gradient to water over 2 minutes. Elution fractions are preferably collected and counted in a scintillation counter to determine elution times of labelled material and coelution with synthetic standards should be assessed.

Phospholipase D activity can also be measured by published techniques (Reinhold et al., 1990).

6. GTP Binding and GTPase Activity of NIP

Certain low MW cytosolic proteins that appear to be important in PMN activation have GTP binding properties.

It is contemplated that NIP could act as a competitive antagonist of these proteins. Certain of the studies described above suggest that NIP activity is dependent on G proteins. The present inventor proposes to examine whether NIP binds GTP in vitro and whether it has GTPase activity.

GTPase activity may be determined by incubating membranes in the presence of [$\gamma^{32}$P]GTP and determining the release of $^{32}$P. GTP binding activity may be determined by carrying out a binding assay, for example, as follows. NIP should be coated at various concentrations to wells of a 96 well plate, then postcoated with BSA. 1 nM GTP[$\gamma^{35}$S] in a standard binding buffer should then be added and binding assessed by washing out unbound GTP and determining the levels of bound GTP by counting each well for radioactivity. The specific nature of the GTP binding will be assessed by performing the same procedure in the presence of excess unlabeled GTPγS.

7. Structure-Function Relationships of NIP and Second Generation Inhibitors

As detailed in Example II, the sequences of the native peptides NIP and NIP-Arg, as purified from bronchoalveolar lavage fluid, contain a potential phosphorylation site comprising serine and tyrosine, and also glycine. Either or both of which serine and tyrosine residues have the potential to become phosphorylated, and NIP and Gly-Ser-Tyr-Phe-Phe (seq id no:3) are shown hereinabove to be actively phosphorylated by PMN lysates. The inventor proposes that phosphorylation of NIP and NIP-like peptides may result in a reduction of their inhibitory actions. To overcome this, the inventor has designed a series of second generation peptides, or analogues, which are contemplated to have enhanced or longer-lasting inhibitory activity.

The improved peptide analogues have sequences based upon the NIP phosphorylation site, namely Gly-Ser-Tyr-Phe-Phe, but contain different residues in place of serine or tyrosine, serine and tyrosine, and also glycine. It is contemplated that these serine, tyrosine or glycine residues may be substituted by any amino acid, but more preferably, by a biologically functional equivalent amino acid which will not significantly alter the other desirable characteristics of the peptide.

Initially, the inventor selected alanine as an appropriate as a substitute for glycine, serine or tyrosine as alanine is a small, neutral amino acid. As such, a substitution employing alanine is highly unlikely to substantially alter the various properties of a peptide other than its ability to become phosphorylated.

The first three of these second generation peptides have been synthesized and examined. As noted previously, these peptides, represented by seq id no:12, seq id no:13 and seq id no:14, have variable effects on PMN chemotaxis and superoxide production. Gly-Ser-Ala-Phe-Phe (seq id no:13) and Gly-Ala-Ala-Phe-Phe (seq id no:12) inhibit fMLP-induced PMN superoxide production more significantly than any other peptides detailed in the present application. In contrast, Gly-Ala-Tyr-Phe-Phe (seq id no:14), and to a lesser extent, Gly-Ala-Ala-Phe-Phe (seq id no:12) more significantly inhibit PMN chemotaxis.

EXAMPLE IV

IN VIVO STUDIES AND TREATMENT PROTOCOLS

This example is directed to the techniques contemplated by the inventor for use in characterizing the in vivo actions of NIP and the use of NIP-based compositions in animal or human treatment protocols.

1. Effects of NIP on Inflammation In Vivo

The inventor proposes to initially examine the ability of NIP to inhibit dermal inflammation by determining its ability to blunt in vivo cellular influx and protein leak in a well described model of dermal inflammation in rabbits. This model is chosen over a model of airway inflammation because of the ease of assessment of inflammation and the amount of previous work dealing with the model (Rampart et al., 1989; and Colditz et al., 1989). However, it is contemplated that a model of airway inflammation will subsequently be utilized to examine the in vivo efficacy of this inhibitor.

In the chosen model, New Zealand albino rabbits may be injected with 10 $\mu$Ci $^{125}$I-labeled human serum albumin through the lateral ear vein. Synthetic NIP (20 $\mu$g protein in 100 $\mu$l buffer) should be injected intradermally followed after one hour by fMLP ($10^{-9}$ moles) or interleukin 8 ($10^{-9}$ moles). Certain sites should be injected with the inhibitor diluent, irrelevant peptide, or agonist alone. About two hours later, full thickness skin samples 1 cm in diameter may be punched out, fixed and stained with Wright-Giemsa or for myeloperoxidase and the histology examined for PMN infiltration, for example, by a modification of a previously described protocol for assessment of subepithelial bronchial inflammation (Cooper et al., 1989). Other skin biopsies may be counted in a gamma counter to assess the amount of albumin flux into the injected skin.

Skin inflammation after administration of the inhibitor in conjunction with FMLP or lipopolysaccharide (see above) should be compared to time-matched agonist-treated or untreated controls. In fact control injections should ideally be performed in the same animal. At least 4 replicates for each experimental arm are recommended. Where multiple groups are involved, differences between groups may be determined by ANOVA.

2. Treatment Protocols

Due to precautions which are necessarily attendant to every new pharmaceutical, the NIP and NIP analogues and compositions of the present invention have not been tested as yet in a clinical setting in human subjects. However, the in vitro activity of NIP in inhibiting PMN activation and chemotaxis is believed to demonstrate the utility of the present invention as an anti-inflammatory agent. The following embodiments are prophetic and represent the best mode contemplated by the present inventor of carrying out the practice of the invention in various clinical settings.

It is believed that pharmaceutical compositions which include NIP, NIP analogues or NIP-based second generation compounds will prove to be useful in the treatment of various inflammatory diseases such as rheumatoid arthritis, inflammatory bowel disease, reperfusion cardiac damage after myocardial infarction. These peptides are thought to be particularly suitable for the inhibition of pulmonary inflammation, such as occurs in asthma, chronic bronchitis aid acute lung injury. However, they may also prove to be useful as anti-proliferative agents to downregulate lymphocyte proliferation, for example, in the treatment of cancer and other diseases and disorders associated with increased cellular proliferation.

For the treatment of asthma and bronchitis, one may use nasal solutions or sprays, aerosols or inhalants. Nasal solutions are usually aqueous solutions designed to be administered to the nasal passages in drops or sprays. Nasal solutions are prepared so that they are similar in many respects to nasal secretions, so that normal ciliary action is maintained. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

Inhalations and inhalants are pharmaceutical preparations designed for delivering a drug or compound into the respiratory tree of a patient. A vapor or mist is administered and reaches the affected area to give relief from symptoms of bronchial and nasal congestion. Inhalations may be administered by the nasal or oral respiratory routes. The administration of inhalation solutions is only effective if the droplets are sufficiently fine and uniform in size so that the mist reaches the bronchioles.

Another group of products, also known as inhalations, and sometimes called insufflations, consists of finely powdered or liquid drugs that are carried into the respiratory passages by the use of special delivery systems, such as pharmaceutical aerosols, that hold a solution or suspension of the drug in a liquefied gas propellant. When released through a suitable valve and oral adapter, a metered does of the inhalation is propelled into the respiratory tract of the patient.

Particle size is of major importance in the administration of this type of preparation. It has been reported that the optimum particle size for penetration into the pulmonary cavity is of the order of 0.5 to 7 $\mu$m. Fine mists are produced by pressurized aerosols and hence their use in considered advantageous.

Asthma or chronic bronchitis due to occupational exposure or smoke inhalation result from chronic inflammation of the airways. Inhalation of one, or a combination, of the molecules described in this application may attenuate this inflammation. The range of doses to be administered by aerosol is estimated to be in the range of about 1 $\mu$g/ml to 100 $\mu$g/ml.

Various other pharmaceutical formulations of NIP are contemplated for use in treating disorders other than those connected with the pulmonary system. These include parenteral formulations, such as those for intravenous, intramuscular, subcutaneous and intraperitoneal administration; formulations for topical use, such as in creams, ointments and gels; and liposome-encapsulated peptides. The precise make-up of these pharmaceutical compositions and carriers will generally be known to those of skill in the art in light of the present disclosure, and are further detailed in *Remington's Pharmaceutical Sciences,* 16th ed., 1980, Mack Publishing Co., incorporated herein by reference.

3. Antibodies

The relative concentration of NIP in tissue may correlate with subsequent development of inflammatory disorders such as bronchitis, acute lung injury, arthritis, inflammatory bowel disease or psoriasis. Previous work with the natural molecule has shown such a correlation, i.e., the degree of bronchitis induced by inhalation of a substance was inversely proportional to the concentration of NIP present in the bronchial secretions prior to the challenge. Therefore, tests to measure concentrations of NIP in the airways, or in other tissues, is contemplated to be of use in disease diagnosis and prognosis. Such diagnostic assays would include the production of antibodies to NIP or related peptides and development of immunoassays.

The development of antibodies to a particular antigen whether polyclonal or monoclonal, are well known in the art and can readily be achieved by skilled immunologists. This is the case even where the particular molecule is not antigenic in and of itself, through either the attachment of an immunostimulating ligand such as keyhole limpet hemocyanin, or by finding a species wherein the molecule is antigenic.

Polyclonal anti-NIP-antibodies can be prepared by immunizing an experimental animal, such as a rabbit. Antisera of this kind can be quantitated by immunodot assay, western blotting, ELISA, RIA, and such like. Monoclonal antibodies may be developed by a number of accepted techniques, for example, as disclosed by U.S. Pat. Nos. 4,172,124 and 4,271,145, both to Koprowski et al., incorporated herein by reference.

For in vitro diagnostic work, for example, in an immunoassay to quantitate NIP levels in biological fluids, such as lavage fluid, an NIP antibody may be used in an ELISA assay which employs the antibody together with an immuno detection reagent capable of detecting quantitatively specific immune complex formation. Immunological techniques such as ELISAa are well known to those of skill in the art, for example, see U.S. Pat. Nos. 4,454,233 and 4,446,232, both incorporated herein by reference. ELISAa may be automated or semi-automated, and employed in immunodetection kits which include immunodetection reagents such as radioactive or enzyme-linked ligands typically associated with either the antibody, antigen or a second antigen or antibody.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background, or teach methodology, techniques, and/or compositions employed herein.

Berkow, R. L., Dodson, M. and Kraft, A. S. Human neutrophils contain distinct cytosolic and particulate tyrosine kinase activities: Possible role in neutrophil activation. *Biochem. Biophys. Acta* 1989;997:292–301.

Bober, E. et al. The muscle regulatory gene, Myf-6, has a biphasic pattern of expression during early mouse development. *J. Cell. Biol.* 113:1255–65,1991.

Brozna, J. P., Senior, R. M., Dreutzer, D. L. and Ward, P. A. 1977. Chemotactic factor inactivators of human granulocytes. *J. Clin. Invest.* 60:1280–1288.

Caldwell, S. E., Cassidy, L. F. and Abramson, J. S. Alterations in cell protein phosphorylation in human neutrophils exposed to influenza A virus. A possible mechanism for depressed cellular end-stage functions. *J. Immunol.* 140:3560–3565, 1988.

Caldwell, S. E., Cassidy, L. F. and Abramson, J. S. Alterations in cell protein phosphorylation in human neutrophils exposed to influenza A virus. A possible mechanism for depressed cellular end-stage functions. *J. Immunol.* 140:3560–3565, 1988.

Cockcroft, S. The role of inositol phospholipid metabolism and diacylglycerol production in neutrophil signal transduction. In *The Neutrophil: Cellular Biochemistry and Physiology* M. B. Hallet Editor, CRC Press 1989.

Colditz, I., Zwahlen, R., Dewald, B. and Baggiolini, M. In vivo inflammatory activity of neutrophil-activating factor, a novel chemotactic peptide derived from human monocytes. *Am. J. Path.* 1989;134:755–760.

Cooper, J. A. D., Jr., Merrill, W. W., Rankin, J. A., Sibille, Y. and Buck, M. G. Bronchoalveolar cell activation and arachidonic acid metabolism after inhalation of a bronchoconstricting agent. *J. Appl. Physiol.* 1988;64:1615–1623.

Cooper, J. A. D., Jr., Merrill, W. W., Buck, M. G. and Schachter, E. N. 1986. The relationship between bronchoalveolar neutrophil recruitment and bronchoconstriction induced by a soluble extract of cotton bracts. *Am. Rev. Respir. Dis.* 134:975–982.

Cooper, J. A. D., Jr., Merrill, W. W. and Buck, M. G. Kinetics of cellular influx and histamine release into normal human bronchi. *Am. J. Physiol.* 257:L277–L283;1989.

Cooper, J. A. D., Jr., Sibille, Y., Zitnik, R., Bayles, G., Buck, M. G. and Merrill, W. W. Isolation of an inhibitor of neutrophil function from bronchial lavage of normal volunteers: Relationship to bronchoconstriction and airway inflammation. *Am. J. Physiol.* 260:L510–L509; 1991.

Cronstein, B. N., Daguma, L., Nichols, D., Hutchison, A. J. and Williams, M. The adenosine/neutrophil paradox resolved: Human neutrophils possess both $A_1$ and $A_2$ receptors that 20 promote chemotaxis and inhibit $O_2$-generation, respectively. *J. Clin. Invest.* 85:115–1157, 1990.

Edelman, A. M., Blumenthal, D. K. and Krebs, E. G. Protein serine/threonine kinases. *Ann. Rev. Biochem.* 1987;56:567–613.

Franklin, C. C., Sanchez, V., Wagner, F., Woodgett, J. R. and Kraft, A. S. Phorbol ester-induced amino terminal phosphorylation of c-Jun but not JunB regulates transcriptional activation. 1991 (Submitted)

Goetzl, E. J. and Austen, K. F. 1972. A neutrophil-immobilizing factor derived from human leukocytes. I. Generation and partial characterization. *J. Exp. Med.* 136:1564–1580.

Gordon, R., Sheppard, D., McDonald, E., Scypiniski, L. and Distefano, S. Airway hyperresponsiveness and inflammation induced by toluene diisocyanate in guinea pigs. *Am. Rev. Respir. Dis.* 132: 1106–1112, 1985.

Ham, E. A., Soderman, D. D., Zanetti, M. E., Dougherty, H. W., McCauley, E. and Kuehl, F. A., Jr. Inhibition by prostaglandins of leukogriene $B_4$ release from activated neutrophils. *Proc. Natl. Acad. Sci.* 80:4349–4353, 1983.

Hartshorn, K. L. and Tauber, A. I. The influenza virus-infected phagocyte. A model of deactivation. *Hematology/Oncology Clinics of North America* 1988;2:301–315.

Haslett, C., Guthree, L. A., Kopaniak, M. M., Johnston, R. B., Jr. and Henson, P. M. Modulation of multiple neutrophil functions by preparative methods or trace concentrations of bacterial lipopolysaccharide. *Am. J. Path.* 119:101–110, 1985.

Holtzman, M. J., Fabbri, L. M., O'Byrne, P. M., Gold, B. D., Aizawa, H., Walters, E. H., Alpert, S. E. and Nadel, J. A. Importance of airway inflammation for hyperresponsiveness induced by ozone. *Am. Rev. Respir. Dis.* 127:686–690, 1983.

Kainoh, M., Imai, R., Umetsu, T., Hattori, M. and Nishio, S. Prostacyclin and beraprost sodium as suppressor of activated rat polymorphonuclear leukocytes. *Biochem. Pharmacol.* 39:477–484,1990.

Kanaho, Y., Nishida, A. and Nozawa, Y. Calcium rather than protein kinase C is the major factor to activate phospholipase D in FMLP-stimulated rabbit peritoneal neutrophils. Possible involvement of calmodulin/myosin L chain kinase pathway. *J. Immunol.* 149(2):622–8, 1992.

Klempner, M. S. and Rocklin, R. E. Effects of leukocyte inhibitory factor (LIF) on human neutrophil function. 1983. *Inflammation* 7:145–153.

Kyte, J. and Doolittle, R. F. A simple method for displaying the hydropathic character of a protein. *J. Mol. Biol.* 157:105–132, 1982).

Pearson, R. B. and Kemp, B. E. Protein kinase phosphorylation site sequences and consensus specificity motifs: Tabulations. *Meth. Enzymology* 200:62–81, 1991.

Rampart, M., De Smet, W., Fiers, W. and Herman, A. G. Inflammatory properties of recombinant tumor necrosis factor in rabbit skin in vivo. *J. Exp. Med.* 1989;169:2227–2232.

Reinhold, S. L., Prescott, S. M., Zimmerman, G. A. and McIntyre, T. M. Activation of human neutrophil phospholipase D by three separable mechanisms. *FASEB J.* 1990;4:208–214.

Ringer, N. I. P. Separation of phosphotyrosine, phosphoserine, and phosphothreonine by high-performance liquid chromatography. Pages 3–8 In: *Methods in Enzymology*. Protein Phosphorylation (Hunter, T., Sefton, B. M., editors) Academic Press 1991.

Robbins, R. A., Rasmussen, J. K., Clayton, M. E. and Gossman, G. L. Antigenic identification of chemotactic factor inactivator in normal human serum and bronchoalveolar lavage fluid. *J. Lab. Clin. Med.* 1987; 110:292–9.

Rossi, F., Grzeskowiak, M. and Kella, Bianca V. Double stimulation with FMLP and Con A restores the activation of the respiratory burst but not of the phosphoinositide turnover in $Ca^{2+}$-depleted human neutrophils. A further example of dissociation between stimulation of the NADPH oxidase and phosphoinositide turnover. *Biochem. Biophys. Res. Comm.* 1986;140:1–11.

Shephard, E. G., Beer, S. M., Anderson, R., Strachan, A. F., Nel, A. E. and DeBeer, F. C. Generation of biologically active C-reactive protein peptides by a neutral protease on the membrane of phorbol myristate acetate-stimulated neutrophils. *J. Immunol.* 143:2974–2981, 1989.

Sibille, Y. and Reynolds, H.Y. State of the art: Macrophages and polymorphonuclear neutrophils in lung disease and injury. *Am. Rev. Respir. Dis.* 1990;141:471–501.

Sibille, Y., Merrill, W. W., Naegel, G. P., Care, S. B. Cooper, J. A. D. Jr, ad Reynolds, H. Y. Human alveolar macrophages release a factor which inhibits phagocyte function. *Am. J. Respir. Cell Mol. Biol.* 1:407–415:1989.

Sklar, L. A. Ligand-receptor dynamics and signal amplification in the neutrophil. *Adv. Immunol.* 1986;39:95.

Snapper, J. R., Brigham, K. L. Inflammation and airway reactivity. *Exp. Lung Res.,* 6:83–89, 1984.

Solley, G. O., Gleich, G. J., Jordon, R. E. and Schroeter, A. L. The late phase of the immediate wheal-and-flare skin reaction. *J. Clin. Invest.* 1976;58:408–413.

Stockley, R. A., Shaw, J., Afford, S. C., Morrison, H. M., Burnett, D. Effect of alpha-1-proteinase inhibitor on neutrophil chemotaxis. *Am. J. Resp. Cell. Mol. Biol.* 2:163–170,1990.

Swank, D. W., Moore, S. B. Roles of the neutrophil and other mediators in adult respiratory distress syndrome. *Mayo Clin. Proc.,* 64:1118–1132, 1989.

Uings, I. J., Thompson, N. T., Randall, R. W., Spacey, G. D., Bonser, R. W., Hudson, A. T., Garland, L. G. Tyrosine phosphorylation is involved in receptor coupling to phospholipase D but not phospholipase C in the human neutrophil. *Biochem. J.,* 281:597–600, 1992.

---

What is claimed is:

1. A method for preparing a phagocyte inhibitor, comprising the steps of
    (a) obtaining bronchoalveolar lavage fluid from an animal;
    (b) subjecting said fluid to fractionation; and
    (c) identifying a fraction containing phagocyte inhibitory activity.

2. The method of claim 1 wherein step (b) comprises subjecting said bronchoalveolar lavage fluid to fractionation according to charge or hydrophobicity.

3. A composition comprising a phagocyte inhibitor, purified relative to its natural state, preparable by the process of claim 1..

4. The composition of claim 3 wherein said composition comprises a peptide having the amino acid sequence Arg-Glu-Gly-Ser-Tyr-Phe-Phe-Gly-Asp-Asn-Ala (SEQ ID NO:1).

5. The composition of claim 3 wherein said composition comprises a peptide having the amino acid sequence Glu-Gly-Ser-Tyr-Phe-Phe-Gly-Asp-Asn-Ala (SEQ ID NO:2).

6. The composition of claim 3 wherein said composition comprises a peptide having the amino acid sequence Gly-Ser-Tyr-Phe-Phe (SEQ ID NO:3).

7. The composition of claim 3 wherein said composition comprises a peptide having the amino acid sequence Arg-Glu-Gly-Ser-Ala-Phe-Phe-Gly-Asp-Asn-Ala (SEQ ID NO:5).

8. The composition of claim 3 wherein said composition comprises a peptide having the amino acid sequence Arg-Glu-Gly-Ala-Tyr-Phe-Phe-Gly-Asp-Asn-Ala (SEQ ID NO:6).

9. The composition of claim 3 wherein said composition comprises a peptide having the amino acid sequence Gly-Ser-Ala-Phe-Phe (SEQ ID NO:13).

10. The composition of claim 3 wherein said composition comprises a peptide having the amino acid sequence Gly-Ala-Tyr-Phe-Phe (SEQ ID NO:14).

11. A method for inhibiting phagocyte activation comprising contacting phagocytes with a peptide of between 5 and 100 amino acids in length including within its sequence an amino acid sequence comprising $AA_1$-$AA_2$-$AA_3$-Phe-Phe wherein (a) $AA_1$ is glycine, alanine, tryptophan, proline, asparagine, glutamine, histidine, cysteine, methionine, valine, leucine, isoleucine, threonine, serine or tyrosine;
    (b) $AA_2$ is serine, alanine, glycine, tryptophan, proline, asparagine, glutamine, histidine, cysteine, methionine, valine, threonine or tyrosine; and
    (c) $AA_3$ is tyrosine, alanine, glycine, tryptophan, proline, histidine, asparagine, glutamine, cysteine, methionine, valine, phenylalanine, leucine, isoleucine, serine or threonine.

12. The method of claim 11 wherein said peptide is administered in vivo.

13. A method for inhibiting phagocyte activation comprising contacting phagocytes with a peptide of between 5 and 100 amino acids in length comprising the amino acid sequence Gly-Ser-Tyr-Phe-Phe (SEQ ID NO:3).

14. A method for inhibiting phagocyte activation comprising contacting phagocytes with a peptide of between 5 and 100 amino acids in length comprising the amino acid sequence Gly-Ser-Ala-Phe-Phe (SEQ ID NO:13).

15. A method for inhibiting phagocyte activation comprising contacting phagocytes with a peptide of between 5 and 100 amino acids in length comprising the amino acid sequence Gly-Ala-Tyr-Phe-Phe (SEQ ID NO:14).

16. A method for inhibiting phagocyte activation comprising contacting phagocytes with a peptide of between 5 and 100 amino acids in length comprising the amino acid sequence Arg-Glu-Gly-Ser-Tyr-Phe-Phe-Gly-Asp-Asn-Ala (SEQ ID NO:1).

17. The method of claims 11, 13, 14, 15 or 16 wherein said peptide is administered in a pharmaceutically acceptable carrier.

18. A method for reducing inflammation in an animal, comprising administering to said animal a peptide of between 5 and about 100 amino acid residues in length including within its sequence an amino acid sequence comprising $AA_1$-$AA_2$-$AA_3$-Phe-Phe wherein (a) $AA_1$ is glycine, alanine, tryptophan, proline, asparagine, glutamine, histidine, cysteine, methionine, valine, leucine, isoleucine, threonine, serine or tyrosine;
    (b) $AA_2$ is serine, alanine, glycine, tryptophan, proline, asparagine, glutamine, histidine, cysteine, methionine, valine, threonine or tyrosine; and (c) AA₃ is tyrosine, alanine, glycine, tryptophan, proline, histidine, asparagine, glutamine, cysteine, methionine, valine, phenylalanine, leucine, isoleucine, serine or threonine.

19. A method for reducing inflammation in an animal, comprising administering to said animal a peptide of between 5 and about 100 amino acid residues in length comprising the amino acid sequence Gly-Ser-Tyr-Phe-Phe (SEQ ID NO:3).

20. A method for reducing inflammation in an animal, comprising administering to said animal a peptide of between 5 and about 100 amino acid residues in length comprising the amino acid sequence Gly-Ser-Ala-Phe-Phe (SEQ ID NO:13).

21. A method for reducing inflammation in an animal, comprising administering to said animal a peptide of between 5 and about 100 amino acid residues in length comprising the amino acid sequence Gly-Ala-Tyr-Phe-Phe (SEQ ID NO:14).

22. A method for reducing inflammation in an animal, comprising administering to said animal a peptide of between 5 and about 100 amino acid residues in length comprising the amino acid sequence Arg-Glu-Gly-Ser-Tyr-Phe-Phe-Gly-Asp-Asn-Ala (SEQ ID NO:1).

23. The method of claims 21 or 22 wherein said peptide is administered in a pharmaceutically acceptable carrier.

* * * * *

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH:     11 amino acid residues
      (B) TYPE:       amino acid
      (C) STRANDEDNESS: single
      (D) TOPOLOGY:   linear (xi) SEQUENCE DESCRIPTION: SEQ ID NO:1:

Arg Glu Gly Ser Tyr Phe Phe Gly Asp Asn Ala
1            5               10

(2) INFORMATION FOR SEQ ID NO:2:

(i) SEQUENCE CHARACTERISTICS:
      (A) LENGTH:     10 amino acid residues
      (B) TYPE:       amino acid
      (C) STRANDEDNESS: single
      (D) TOPOLOGY:   linear (xi) SEQUENCE DESCRIPTION: SEQ ID NO:2:

Glu Gly Ser Tyr Phe Phe Gly Asp Asn Ala
1          5             10

(2) INFORMATION FOR SEQ ID NO:3:

(i) SEQUENCE CHARACTERISTICS:
        (A) LENGTH:        5 amino acid residues
        (B) TYPE:          amino acid
        (C) STRANDEDNESS: single
        (D) TOPOLOGY:     linear (xi) SEQUENCE DESCRIPTION: SEQ ID NO:3:

Gly Ser Tyr Phe Phe
1              5

(2) INFORMATION FOR SEQ ID NO:4:

(i) SEQUENCE CHARACTERISTICS:
        (A) LENGTH:        11 amino acid residues
        (B) TYPE:          amino acid
        (C) STRANDEDNESS: single
        (D) TOPOLOGY:     linear (xi) SEQUENCE DESCRIPTION: SEQ ID NO:4:

Arg Glu Gly Ala Ala Phe Phe Gly Asp Asn Ala
1              5                  10

(2) INFORMATION FOR SEQ ID NO:5:

(i) SEQUENCE CHARACTERISTICS:
        (A) LENGTH:        11 amino acid residues
        (B) TYPE:          amino acid
        (C) STRANDEDNESS: single
        (D) TOPOLOGY:     linear (xi) SEQUENCE DESCRIPTION: SEQ ID NO:5:

Arg Glu Gly Ser Ala Phe Phe Gly Asp Asn Ala
1              5                  10

(2) INFORMATION FOR SEQ ID NO:6:

(i) SEQUENCE CHARACTERISTICS:
        (A) LENGTH:        11 amino acid residues
        (B) TYPE:          amino acid
        (C) STRANDEDNESS: single
        (D) TOPOLOGY:     linear (xi) SEQUENCE DESCRIPTION: SEQ ID NO:6:

Arg Glu Gly Ala Tyr Phe Phe Gly Asp Asn Ala
1              5                  10

(2) INFORMATION FOR SEQ ID NO:7:

(i) SEQUENCE CHARACTERISTICS:
        (A) LENGTH:        11 amino acid residues
        (B) TYPE:          amino acid
        (C) STRANDEDNESS: single
        (D) TOPOLOGY:     linear (xi) SEQUENCE DESCRIPTION: SEQ ID NO:7:

Arg Glu Ala Ser Tyr Phe Phe Gly Asp Asn Ala
1              5                  10

(2) INFORMATION FOR SEQ ID NO:8:

(i) SEQUENCE CHARACTERISTICS:
        (A) LENGTH:        10 amino acid residues
        (B) TYPE:          amino acid
        (C) STRANDEDNESS: single
        (D) TOPOLOGY:     linear (xi) SEQUENCE DESCRIPTION: SEQ ID NO:8:

```
Glu Gly Ala Ala Phe Phe Gly Asp Asn Ala
  1               5                  10
```

(2) INFORMATION FOR SEQ ID NO:9:

(i) SEQUENCE CHARACTERISTICS:
        (A) LENGTH:       10 amino acid residues
        (B) TYPE:         amino acid
        (C) STRANDEDNESS: single
        (D) TOPOLOGY:     linear (xi) SEQUENCE DESCRIPTION: SEQ ID NO:9:

```
Glu Gly Ser Ala Phe Phe Gly Asp Asn Ala
  1               5                  10
```

(2) INFORMATION FOR SEQ ID NO:10:

(i) SEQUENCE CHARACTERISTICS:
        (A) LENGTH:       10 amino acid residues
        (B) TYPE:         amino acid
        (C) STRANDEDNESS: single
        (D) TOPOLOGY:     linear (xi) SEQUENCE DESCRIPTION: SEQ ID NO:10:

```
Glu Gly Ala Tyr Phe Phe Gly Asp Asn Ala
  1               5                  10
```

(2) INFORMATION FOR SEQ ID NO:11:

(i) SEQUENCE CHARACTERISTICS:
        (A) LENGTH:       11 amino acid residues
        (B) TYPE:         amino acid
        (C) STRANDEDNESS: single
        (D) TOPOLOGY:     linear (xi) SEQUENCE DESCRIPTION: SEQ ID NO:11:

```
Glu Ala Ser Tyr Phe Phe Gly Asp Asn Ala
  1               5                  10
```

(2) INFORMATION FOR SEQ ID NO:12:

(i) SEQUENCE CHARACTERISTICS:
        (A) LENGTH:       5 amino acid residues
        (B) TYPE:         amino acid
        (C) STRANDEDNESS: single
        (D) TOPOLOGY:     linear (xi) SEQUENCE DESCRIPTION: SEQ ID NO: 12:

```
Gly Ala Ala Phe Phe
  1               5
```

(2) INFORMATION FOR SEQ ID NO:13:

(i) SEQUENCE CHARACTERISTICS:
        (A) LENGTH:       5 amino acid residues
        (B) TYPE:         amino acid
        (C) STRANDEDNESS: single
        (D) TOPOLOGY:     linear (xi) SEQUENCE DESCRIPTION: SEQ ID NO:13:

```
Gly Ser Ala Phe Phe
  1               5
```

(2) INFORMATION FOR SEQ ID NO:14:

(i) SEQUENCE CHARACTERISTICS:
        (A) LENGTH:       5 amino acid residues
        (B) TYPE:         amino acid

```
            (C) STRANDEDNESS:   single
            (D) TOPOLOGY:       linear (xi) SEQUENCE DESCRIPTION: SEQ ID NO:14:

Gly Ala Tyr Phe Phe
1               5

(2) INFORMATION FOR SEQ ID NO:15:

(i) SEQUENCE CHARACTERISTICS:
            (A) LENGTH:         5 amino acid residues
            (B) TYPE:           amino acid
            (C) STRANDEDNESS:   single
            (D) TOPOLOGY:       linear (xi) SEQUENCE DESCRIPTION: SEQ ID NO:15:

Ala Ser Tyr Phe Phe
1               5

(2) INFORMATION FOR SEQ ID NO:16:

(i) SEQUENCE CHARACTERISTICS:
            (A) LENGTH:         11 amino acid residues
            (B) TYPE:           amino acid
            (C) STRANDEDNESS:   single
            (D) TOPOLOGY:       linear (xi) SEQUENCE DESCRIPTION: SEQ ID NO:16:

Asn Glu Gly Ser Tyr Phe Phe Gly Asp Asn Ala
1               5                   10

(2) INFORMATION FOR SEQ ID NO:17:

(i) SEQUENCE CHARACTERISTICS:
            (A) LENGTH:         11 amino acid residues
            (B) TYPE:           amino acid
            (C) STRANDEDNESS:   single
            (D) TOPOLOGY:       linear (xi) SEQUENCE DESCRIPTION: SEQ ID NO:17:

Asn Glu Gly Ala Ala Phe Phe Gly Asp Asn Ala
1               5                   10

(2) INFORMATION FOR SEQ ID NO:18:

(i) SEQUENCE CHARACTERISTICS:
            (A) LENGTH:         11 amino acid residues
            (B) TYPE:           amino acid
            (C) STRANDEDNESS:   single
            (D) TOPOLOGY:       linear (xi) SEQUENCE DESCRIPTION: SEQ ID NO:18:

Asn Glu Gly Ser Ala Phe Phe Gly Asp Asn Ala
1               5                   10

(2) INFORMATION FOR SEQ ID NO:19:

(i) SEQUENCE CHARACTERISTICS:
            (A) LENGTH:         11 amino acid residues
            (B) TYPE:           amino acid
            (C) STRANDEDNESS:   single
            (D) TOPOLOGY:       linear (xi) SEQUENCE DESCRIPTION: SEQ ID NO:19:

Asn Glu Gly Ala Tyr Phe Phe Gly Asp Asn Ala
1               5                   10

(2) INFORMATION FOR SEQ ID NO:20:
```

```
      (i) SEQUENCE CHARACTERISTICS:
            (A) LENGTH:         11 amino acid residues
            (B) TYPE:           amino acid
            (C) STRANDEDNESS:   single
            (D) TOPOLOGY:       linear (xi) SEQUENCE DESCRIPTION: SEQ ID NO:20:

Asn Glu Ala Ser Tyr Phe Phe Gly Asp Asn Ala
 1               5                   10

(2) INFORMATION FOR SEQ ID NO:21:

(i) SEQUENCE CHARACTERISTICS:
            (A) LENGTH:         11 amino acid residues
            (B) TYPE:           amino acid
            (C) STRANDEDNESS:   single
            (D) TOPOLOGY:       linear (xi) SEQUENCE DESCRIPTION: SEQ ID NO:21:

Ser Asn Arg Gly Phe Ala Tyr Phe Asp Glu Gly
 1               5                   10
```